(12) United States Patent
Boysen et al.

(10) Patent No.: US 10,647,749 B2
(45) Date of Patent: May 12, 2020

(54) **GLYCOSYLATED YGHJ POLYPEPTIDES FROM ENTEROTOXIGENIC *ESCHERICHIA COLI* (ETEC)**

(71) Applicants: Syddansk Universitet, Odense M (DK); Aarhus Universitet, Aarhus C (DK)

(72) Inventors: Anders Boysen, Odense SØ (DK); Jakob Møller-Jensen, Odense M (DK); Giuseppe Palmisano, Turi (IT); Martin Røssel Larsen, Odense S (DK)

(73) Assignees: Syddansk Universitet, Odense M (DK); Aarhus Universitet, Aarhus C (DK)

( * ) Notice: Subject to any disclaimer, the term of this patent is extended or adjusted under 35 U.S.C. 154(b) by 0 days.

(21) Appl. No.: 16/392,406

(22) Filed: Apr. 23, 2019

(65) Prior Publication Data

US 2019/0322706 A1 Oct. 24, 2019

Related U.S. Application Data

(62) Division of application No. 15/766,209, filed as application No. PCT/DK2016/060321 on Oct. 6, 2016.

(30) Foreign Application Priority Data

Oct. 6, 2015 (EP) .................................. 15188608

(51) Int. Cl.
*C07K 14/245* (2006.01)
*A61K 39/108* (2006.01)

(52) U.S. Cl.
CPC ........ *C07K 14/245* (2013.01); *A61K 39/0258* (2013.01); *Y02A 50/474* (2018.01)

(58) Field of Classification Search
None
See application file for complete search history.

(56) References Cited

FOREIGN PATENT DOCUMENTS

| WO | WO 2009/104092 | 8/2009 |
| WO | WO 2011/007257 | 1/2011 |
| WO | WO 2014/102694 | 7/2014 |
| WO | WO 2015/154783 | 10/2015 |

OTHER PUBLICATIONS

Boysen et al. "A novel mass spectrometric strategy "BEMAP" reveals Extensive O-linked protein glycosylation in Enterotoxigenic *Escherichia coli*" Scientific Reports, 6:32016, pp. 1-13, Aug. 26, 2016.
Parker et al. "Purification and Identification of O—GlcNAc-Modified Peptides Using Phosphate-Based Alkyne CLICK Chemistry in Combination with Titanium Dioxide Chromatography and Mass Spectrometry" Journal of Proteome Research, 2011, 10, pp. 1449-1458.
Wells et al. "Mapping Sites of O—GlcNAc Modification Using Affinity Tags for Serine and Threonine Post-translational Modifications" Molecular & Cellular Proteomics 1.10, pp. 791-804, 2002.
Antonets et al., "Proteomic analysis of *Escherichia coli* protein fractions resistant to solubilization by ionic detergents," Biochemistry, Feb. 2016, 81(1):34-46.
Boysen et al., "SILAC-based comparative analysis of pathogenic *Escherichia coli* secretomes," Journal of Microbiological Methods, Jul. 2015, 116:66-79.
Chou et al., "Biological sequence motif discovery using motif-x," Current Protocols in Bioinformatics, Sep. 2011, DOI: 10.1002/0471250953.bi1315s35.
Knudsen et al., "Effect of glycosylation on the extracellular domain of the Ag43 bacterial autotransporter: enhanced stability and reduced cellular aggregation," Biochemical Journal, Jun. 2008, 412(3):563-577.
Pearson et al., "Improved tools for biological sequence comparison," Proceedings of the National Academy of Sciences, Apr. 1988, 85(8):2444-2448.
Thingholm et al., "Highly selective enrichment of phosphorylated peptides using titanium dioxide," Nature Protocols, Nov. 2006, 1(4):1929-1935.
Thompson et al., "Clustal W: improving the sensitivity of progressive multiple sequence alignment through sequence weighting, position-specific gap penalties and weight matrix choice," Nucleic Acids Research, Nov. 1994, 22(22):4673-4680.
International Search Report and Written Opinion dated Dec. 19, 2016 for PCT/DK2016/050321, filed Oct. 6, 2016.

*Primary Examiner* — Brian Gangle
(74) *Attorney, Agent, or Firm* — Knobbe Martens Olson & Bear LLP

(57) ABSTRACT

The present invention relates to glycosylated YghJ polypeptides from or derived from enterotoxigenic *Escherichia coli* (ETEC) that are immunogenic. In particular, the present invention relates to compositions or vaccines comprising the polypeptides and their application in immunization, vaccination, treatment and diagnosis of ETEC.

16 Claims, 3 Drawing Sheets
Specification includes a Sequence Listing.

SEQUENCE LISTING

<160> NUMBER OF SEQ ID NOS: 51

<210> SEQ ID NO 1

<211> LENGTH: 1519
<212> TYPE: PRT
<213> ORGANISM: Escherichia coli

<400> SEQUENCE: 1

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
            20                  25                  30

Ser Asp Thr Pro Pro Val Asp Ser Gly Thr Gly Ser Leu Pro Glu Val
            35                  40                  45

Lys Pro Asp Pro Thr Pro Asn Pro Glu Pro Thr Pro Glu Pro Thr Pro
50                  55                  60

Asp Pro Glu Pro Thr Pro Glu Pro Ile Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
            100                 105                 110

Asp Gly Phe Thr Phe Lys Pro Gly Glu Asp Val Thr Cys Val Ala Gly
            115                 120                 125

Asn Thr Thr Ile Ala Thr Phe Asn Thr Gln Ser Glu Ala Ala Arg Ser
130                 135                 140

Leu Arg Ala Val Glu Lys Val Ser Phe Ser Leu Glu Asp Ala Gln Glu
145                 150                 155                 160

Leu Ala Gly Ser Asp Asp Lys Lys Ser Asn Ala Val Ser Leu Val Thr
                165                 170                 175

Ser Ser Asn Ser Cys Pro Ala Asn Thr Glu Gln Val Cys Leu Thr Phe
            180                 185                 190

Ser Ser Val Ile Glu Ser Lys Arg Phe Asp Ser Leu Tyr Lys Gln Ile
            195                 200                 205

Asp Leu Ala Pro Glu Glu Phe Lys Lys Leu Val Asn Glu Glu Val Glu
210                 215                 220

Asn Asn Ala Ala Thr Asp Lys Ala Pro Ser Thr His Thr Ser Pro Val
225                 230                 235                 240

Val Pro Val Thr Thr Pro Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
            260                 265                 270

Ile Leu Ser Glu Gly Arg Leu Val Asp Ser Gln Gly Tyr Gly Val Ala
            275                 280                 285

Gly Val Asn Tyr Tyr Thr Asn Ser Gly Arg Gly Val Thr Gly Glu Asn
290                 295                 300

Gly Glu Phe Ser Phe Ser Trp Gly Glu Ala Ile Ser Phe Gly Ile Asp
305                 310                 315                 320

Thr Phe Glu Leu Gly Ser Val Arg Gly Asn Lys Ser Thr Ile Ala Leu
                325                 330                 335

Thr Glu Leu Gly Asp Glu Val Arg Gly Ala Asn Ile Asp Gln Leu Ile
            340                 345                 350

His Arg Tyr Ser Thr Thr Gly Gln Asn Asn Thr Arg Val Val Pro Asp
            355                 360                 365

Asp Val Arg Lys Val Phe Ala Glu Tyr Pro Asn Val Ile Asn Glu Ile
370                 375                 380

Ile Asn Leu Ser Leu Ser Asn Gly Ala Thr Leu Gly Glu Gly Glu Gln

-continued

```
              385                 390                 395                 400
Val Val Asn Leu Pro Asn Glu Phe Ile Glu Gln Phe Asn Thr Gly Gln
                    405                 410                 415
Ala Lys Glu Ile Asp Thr Ala Ile Cys Ala Lys Thr Asp Gly Cys Asn
                    420                 425                 430
Glu Ala Arg Trp Phe Ser Leu Thr Thr Arg Asn Val Asn Asp Gly Gln
                    435                 440                 445
Ile Gln Gly Val Ile Asn Lys Leu Trp Gly Val Asp Thr Asn Tyr Lys
                    450                 455                 460
Ser Val Ser Lys Phe His Val Phe His Asp Ser Thr Asn Phe Tyr Gly
465                 470                 475                 480
Ser Thr Gly Asn Ala Arg Gly Gln Ala Val Val Asn Ile Ser Asn Ala
                    485                 490                 495
Ala Phe Pro Ile Leu Met Ala Arg Asn Asp Lys Asn Tyr Trp Leu Ala
                    500                 505                 510
Phe Gly Glu Lys Arg Ala Trp Asp Lys Asn Glu Leu Ala Tyr Ile Thr
                    515                 520                 525
Glu Ala Pro Ser Ile Val Arg Pro Glu Asn Val Thr Arg Glu Thr Ala
                    530                 535                 540
Ser Phe Asn Leu Pro Phe Ile Ser Leu Gly Gln Val Gly Asp Gly Lys
545                 550                 555                 560
Leu Met Val Ile Gly Asn Pro His Tyr Asn Ser Ile Leu Arg Cys Pro
                    565                 570                 575
Asn Gly Tyr Ser Trp Asn Gly Val Asn Lys Asp Gly Gln Cys Thr
                    580                 585                 590
Leu Asn Ser Asp Pro Asp Asp Met Lys Asn Phe Met Glu Asn Val Leu
                    595                 600                 605
Arg Tyr Leu Ser Asn Asp Arg Trp Leu Pro Asp Ala Lys Ser Ser Met
                    610                 615                 620
Thr Val Gly Thr Asn Leu Glu Thr Val Tyr Phe Lys Lys His Gly Gln
625                 630                 635                 640
Val Leu Gly Asn Ser Ala Pro Phe Ala Phe His Lys Asp Phe Thr Gly
                    645                 650                 655
Ile Thr Val Lys Pro Met Thr Ser Tyr Gly Asn Leu Asn Pro Asp Glu
                    660                 665                 670
Val Pro Leu Leu Ile Leu Asn Gly Phe Glu Tyr Val Thr Gln Trp Gly
                    675                 680                 685
Ser Asp Pro Tyr Ser Ile Pro Leu Arg Ala Asp Thr Ser Lys Pro Lys
                    690                 695                 700
Leu Thr Gln Gln Asp Val Thr Asp Leu Ile Ala Tyr Met Asn Lys Gly
705                 710                 715                 720
Gly Ser Val Leu Ile Met Glu Asn Val Met Ser Asn Leu Lys Glu Glu
                    725                 730                 735
Ser Ala Ser Gly Phe Val Arg Leu Leu Asp Ala Ala Gly Leu Ser Met
                    740                 745                 750
Ala Leu Asn Lys Ser Val Val Asn Asn Asp Pro Gln Gly Tyr Pro Asp
                    755                 760                 765
Arg Val Arg Gln Arg Arg Ser Thr Pro Ile Trp Val Tyr Glu Arg Tyr
                    770                 775                 780
Pro Ala Val Asp Gly Lys Pro Pro Tyr Thr Ile Asp Asp Thr Thr Lys
785                 790                 795                 800
Glu Val Ile Trp Lys Tyr Gln Gln Glu Asn Lys Pro Asp Asp Lys Pro
                    805                 810                 815
```

```
Lys Leu Glu Val Ala Ser Trp Gln Glu Glu Val Gly Lys Gln Val
            820                 825                 830

Thr Gln Phe Ala Phe Ile Asp Glu Ala Asp His Lys Thr Pro Glu Ser
            835                 840                 845

Leu Ala Ala Ala Lys Gln Arg Ile Leu Asp Ala Phe Pro Gly Leu Glu
        850                 855                 860

Val Cys Lys Asp Ser Asp Tyr His Tyr Glu Val Asn Cys Leu Glu Tyr
865                 870                 875                 880

Arg Pro Gly Thr Asp Val Pro Val Thr Gly Met Tyr Val Pro Gln
                885                 890                 895

Tyr Thr Gln Leu Asp Leu Ser Ala Asp Thr Ala Lys Ala Met Leu Gln
            900                 905                 910

Ala Ala Asp Leu Gly Thr Asn Ile Gln Arg Leu Tyr Gln His Glu Leu
        915                 920                 925

Tyr Phe Arg Thr Asn Gly Arg Gln Gly Glu Arg Leu Asn Ser Val Asp
        930                 935                 940

Leu Glu Arg Leu Tyr Gln Asn Met Ser Val Trp Leu Trp Asn Glu Thr
945                 950                 955                 960

Lys Tyr Arg Tyr Glu Glu Gly Lys Glu Asp Glu Leu Gly Phe Lys Thr
                965                 970                 975

Phe Thr Glu Phe Leu Asn Cys Tyr Thr Asn Asn Ala Tyr Val Gly Thr
                980                 985                 990

Gln Cys Ser Ala Glu Leu Lys Lys Ser Leu Ile Asp Asn Lys Met Ile
        995                 1000                1005

Tyr Gly Glu Glu Ser Ser Lys Ala Gly Met Met Asn Pro Ser Tyr
    1010                1015                1020

Pro Leu Asn Tyr Met Glu Lys Pro Leu Thr Arg Leu Met Leu Gly
    1025                1030                1035

Arg Ser Trp Trp Asp Leu Asn Ile Lys Val Asp Val Glu Lys Tyr
    1040                1045                1050

Pro Gly Val Val Asn Thr Asn Gly Glu Thr Val Thr Gln Asn Ile
    1055                1060                1065

Asn Leu Tyr Ser Ala Pro Thr Lys Trp Phe Ala Gly Asn Met Gln
    1070                1075                1080

Ser Thr Gly Leu Trp Ala Pro Ala Gln Gln Glu Val Ser Ile Glu
    1085                1090                1095

Ser Lys Ser Thr Val Pro Val Thr Val Thr Val Ala Leu Ala Asp
    1100                1105                1110

Asp Leu Thr Gly Arg Glu Lys His Glu Val Ser Leu Asn Arg Pro
    1115                1120                1125

Pro Arg Val Thr Lys Thr Tyr Asp Leu Lys Ala Asn Asp Lys Val
    1130                1135                1140

Thr Phe Lys Val Pro Tyr Gly Gly Leu Ile Tyr Ile Lys Gly Asp
    1145                1150                1155

Ser Lys Glu Val Gln Ser Ala Asp Phe Thr Phe Thr Gly Val Val
    1160                1165                1170

Lys Ala Pro Phe Tyr Lys Asp Gly Lys Trp Gln His Asp Leu Asn
    1175                1180                1185

Ser Pro Ala Pro Leu Gly Glu Leu Glu Ser Ala Ser Phe Val Tyr
    1190                1195                1200

Thr Thr Pro Lys Lys Asn Leu Asn Ala Ser Asn Tyr Thr Gly Gly
    1205                1210                1215
```

-continued

Leu Glu Gln Phe Ala Asn Asp Leu Asp Thr Phe Ala Ser Ser Met
1220                1225                1230

Asn Asp Phe Tyr Gly Arg Asp Ser Glu Asp Gly Lys His Arg Met
     1235                1240                1245

Phe Thr Tyr Lys Asn Leu Pro Gly His Lys His Arg Phe Ala Asn
     1250                1255                1260

Asp Val Gln Ile Ser Ile Gly Asp Ala His Ser Gly Tyr Pro Val
     1265                1270                1275

Met Asn Ser Ser Phe Ser Pro Asn Ser Thr Thr Leu Pro Thr Thr
     1280                1285                1290

Pro Leu Asn Asp Trp Leu Ile Trp His Glu Val Gly His Asn Ala
     1295                1300                1305

Ala Glu Thr Pro Leu Thr Val Pro Gly Ala Thr Glu Val Ala Asn
     1310                1315                1320

Asn Val Leu Ala Leu Tyr Met Gln Asp Arg Tyr Leu Gly Lys Met
     1325                1330                1335

Asn Arg Val Ala Asp Asp Ile Thr Val Ala Pro Glu Tyr Leu Glu
     1340                1345                1350

Glu Ser Asn Gly Gln Ala Trp Ala Arg Gly Gly Ala Gly Asp Arg
     1355                1360                1365

Leu Leu Met Tyr Ala Gln Leu Lys Glu Trp Ala Glu Lys Asn Phe
     1370                1375                1380

Asp Ile Lys Lys Trp Tyr Pro Asp Gly Thr Pro Leu Pro Glu Phe
     1385                1390                1395

Tyr Ser Glu Arg Glu Gly Met Lys Gly Trp Asn Leu Phe Gln Leu
     1400                1405                1410

Met His Arg Lys Ala Arg Gly Asp Glu Val Ser Asn Asp Lys Phe
     1415                1420                1425

Gly Gly Lys Asn Tyr Cys Ala Glu Ser Asn Gly Asn Ala Ala Asp
     1430                1435                1440

Thr Leu Met Leu Cys Ala Ser Trp Val Ala Gln Thr Asp Leu Ser
     1445                1450                1455

Glu Phe Phe Lys Lys Trp Asn Pro Gly Ala Asn Ala Tyr Gln Leu
     1460                1465                1470

Pro Gly Ala Ser Glu Met Ser Phe Glu Gly Gly Val Ser Gln Ser
     1475                1480                1485

Ala Tyr Asn Thr Leu Ala Ser Leu Asp Leu Pro Lys Pro Glu Gln
     1490                1495                1500

Gly Pro Glu Thr Ile Asn Gln Val Thr Glu His Lys Met Ser Ala
     1505                1510                1515

Glu

<210> SEQ ID NO 2
<211> LENGTH: 10
<212> TYPE: PRT
<213> ORGANISM: Escherichia coli

<400> SEQUENCE: 2

Tyr Ser Thr Thr Gly Gln Asn Asn Thr Arg
1               5                   10

<210> SEQ ID NO 3
<211> LENGTH: 6
<212> TYPE: PRT
<213> ORGANISM: Escherichia coli

```
<400> SEQUENCE: 3

Tyr Leu Ser Asn Asp Arg
1               5

<210> SEQ ID NO 4
<211> LENGTH: 22
<212> TYPE: PRT
<213> ORGANISM: Escherichia coli

<400> SEQUENCE: 4

Asp Gly Gln Cys Thr Leu Asn Ser Asp Pro Asp Asp Met Lys Asn Phe
1               5                  10                  15

Met Glu Asn Val Leu Arg
            20

<210> SEQ ID NO 5
<211> LENGTH: 22
<212> TYPE: PRT
<213> ORGANISM: Escherichia coli

<400> SEQUENCE: 5

Val Ala Asp Asp Ile Thr Val Ala Pro Glu Tyr Leu Glu Glu Ser Asn
1               5                  10                  15

Gly Gln Ala Trp Ala Arg
            20

<210> SEQ ID NO 6
<211> LENGTH: 29
<212> TYPE: PRT
<213> ORGANISM: Escherichia coli

<400> SEQUENCE: 6

Val Asp Val Glu Lys Tyr Pro Gly Val Val Asn Thr Asn Gly Glu Thr
1               5                  10                  15

Val Thr Gln Asn Ile Asn Leu Tyr Ser Ala Pro Thr Lys
            20                  25

<210> SEQ ID NO 7
<211> LENGTH: 42
<212> TYPE: PRT
<213> ORGANISM: Escherichia coli

<400> SEQUENCE: 7

Val Thr Gly Ala Thr Cys Asn Gly Glu Ser Ser Asp Gly Phe Thr Phe
1               5                  10                  15

Lys Pro Gly Glu Asp Val Thr Cys Val Ala Gly Asn Thr Thr Ile Ala
            20                  25                  30

Thr Phe Asn Thr Gln Ser Glu Ala Ala Arg
        35                  40

<210> SEQ ID NO 8
<211> LENGTH: 13
<212> TYPE: PRT
<213> ORGANISM: Escherichia coli

<400> SEQUENCE: 8

Gln Leu Ile His Arg Tyr Ser Thr Thr Gly Gln Asn Asn
1               5                  10

<210> SEQ ID NO 9
<211> LENGTH: 13
<212> TYPE: PRT
```

<213> ORGANISM: Escherichia coli

<400> SEQUENCE: 9

Ile His Arg Tyr Ser Thr Thr Gly Gln Asn Asn Thr Arg
1               5                   10

<210> SEQ ID NO 10
<211> LENGTH: 13
<212> TYPE: PRT
<213> ORGANISM: Escherichia coli

<400> SEQUENCE: 10

Thr Thr Gly Gln Asn Asn Thr Arg Val Val Pro Asp Asp
1               5                   10

<210> SEQ ID NO 11
<211> LENGTH: 13
<212> TYPE: PRT
<213> ORGANISM: Escherichia coli

<400> SEQUENCE: 11

Asn Val Leu Arg Tyr Leu Ser Asn Asp Arg Trp Leu Pro
1               5                   10

<210> SEQ ID NO 12
<211> LENGTH: 13
<212> TYPE: PRT
<213> ORGANISM: Escherichia coli

<400> SEQUENCE: 12

Gly Gln Cys Thr Leu Asn Ser Asp Pro Asp Asp Met Lys
1               5                   10

<210> SEQ ID NO 13
<211> LENGTH: 13
<212> TYPE: PRT
<213> ORGANISM: Escherichia coli

<400> SEQUENCE: 13

Pro Glu Tyr Leu Glu Glu Ser Asn Gly Gln Ala Trp Ala
1               5                   10

<210> SEQ ID NO 14
<211> LENGTH: 13
<212> TYPE: PRT
<213> ORGANISM: Escherichia coli

<400> SEQUENCE: 14

Tyr Pro Gly Val Val Asn Thr Asn Gly Glu Thr Val Thr
1               5                   10

<210> SEQ ID NO 15
<211> LENGTH: 13
<212> TYPE: PRT
<213> ORGANISM: Escherichia coli

<400> SEQUENCE: 15

Val Asn Thr Asn Gly Glu Thr Val Thr Gln Asn Ile Asn
1               5                   10

<210> SEQ ID NO 16
<211> LENGTH: 13
<212> TYPE: PRT
<213> ORGANISM: Escherichia coli

```
<400> SEQUENCE: 16

Thr Asn Gly Glu Thr Val Thr Gln Asn Ile Asn Leu Tyr
1               5                   10

<210> SEQ ID NO 17
<211> LENGTH: 13
<212> TYPE: PRT
<213> ORGANISM: Escherichia coli

<400> SEQUENCE: 17

Gly Gly Ser Gln Arg Val Thr Gly Ala Thr Cys Asn Gly
1               5                   10

<210> SEQ ID NO 18
<211> LENGTH: 13
<212> TYPE: PRT
<213> ORGANISM: Escherichia coli

<400> SEQUENCE: 18

Gln Arg Val Thr Gly Ala Thr Cys Asn Gly Glu Ser Ser
1               5                   10

<210> SEQ ID NO 19
<211> LENGTH: 13
<212> TYPE: PRT
<213> ORGANISM: Escherichia coli

<400> SEQUENCE: 19

Ala Thr Cys Asn Gly Glu Ser Ser Asp Gly Phe Thr Phe
1               5                   10

<210> SEQ ID NO 20
<211> LENGTH: 13
<212> TYPE: PRT
<213> ORGANISM: Escherichia coli

<400> SEQUENCE: 20

Thr Cys Asn Gly Glu Ser Ser Asp Gly Phe Thr Phe Lys
1               5                   10

<210> SEQ ID NO 21
<211> LENGTH: 13
<212> TYPE: PRT
<213> ORGANISM: Escherichia coli

<400> SEQUENCE: 21

Glu Ser Ser Asp Gly Phe Thr Phe Lys Pro Gly Glu Asp
1               5                   10

<210> SEQ ID NO 22
<211> LENGTH: 13
<212> TYPE: PRT
<213> ORGANISM: Escherichia coli

<400> SEQUENCE: 22

Lys Pro Gly Glu Asp Val Thr Cys Val Ala Gly Asn Thr
1               5                   10

<210> SEQ ID NO 23
<211> LENGTH: 13
<212> TYPE: PRT
<213> ORGANISM: Escherichia coli

<400> SEQUENCE: 23
```

```
Thr Cys Val Ala Gly Asn Thr Thr Ile Ala Thr Phe Asn
1               5                   10
```

<210> SEQ ID NO 24
<211> LENGTH: 11
<212> TYPE: PRT
<213> ORGANISM: Escherichia coli

<400> SEQUENCE: 24

```
Thr Gly Tyr Leu Thr Leu Gly Gly Ser Gln Arg
1               5                   10
```

<210> SEQ ID NO 25
<211> LENGTH: 24
<212> TYPE: PRT
<213> ORGANISM: Escherichia coli

<400> SEQUENCE: 25

```
Ser Leu Arg Ala Val Glu Lys Val Ser Phe Ser Leu Glu Asp Ala Gln
1               5                   10                  15

Glu Leu Ala Gly Ser Asp Asp Lys
            20
```

<210> SEQ ID NO 26
<211> LENGTH: 31
<212> TYPE: PRT
<213> ORGANISM: Escherichia coli

<400> SEQUENCE: 26

```
Ser Asn Ala Val Ser Leu Val Thr Ser Ser Asn Ser Cys Pro Ala Asn
1               5                   10                  15

Thr Glu Gln Val Cys Leu Thr Phe Ser Ser Val Ile Glu Ser Lys
            20                  25                  30
```

<210> SEQ ID NO 27
<211> LENGTH: 14
<212> TYPE: PRT
<213> ORGANISM: Escherichia coli

<400> SEQUENCE: 27

```
Leu Val Asn Glu Glu Val Glu Asn Asn Ala Ala Thr Asp Lys
1               5                   10
```

<210> SEQ ID NO 28
<211> LENGTH: 17
<212> TYPE: PRT
<213> ORGANISM: Escherichia coli

<400> SEQUENCE: 28

```
Glu Ile Asp Thr Ala Ile Cys Ala Lys Thr Gly Cys Asn Glu Ala
1               5                   10                  15

Arg
```

<210> SEQ ID NO 29
<211> LENGTH: 15
<212> TYPE: PRT
<213> ORGANISM: Escherichia coli

<400> SEQUENCE: 29

```
Thr Asp Gly Cys Asn Glu Ala Arg Trp Phe Ser Leu Thr Thr Arg
1               5                   10                  15
```

<210> SEQ ID NO 30

```
<211> LENGTH: 13
<212> TYPE: PRT
<213> ORGANISM: Escherichia coli

<400> SEQUENCE: 30

Leu Trp Gly Val Asp Thr Asn Tyr Lys Ser Val Ser Lys
1               5                   10

<210> SEQ ID NO 31
<211> LENGTH: 18
<212> TYPE: PRT
<213> ORGANISM: Escherichia coli

<400> SEQUENCE: 31

Phe His Val Phe His Asp Ser Thr Asn Phe Tyr Gly Ser Thr Gly Asn
1               5                   10                  15

Ala Arg

<210> SEQ ID NO 32
<211> LENGTH: 18
<212> TYPE: PRT
<213> ORGANISM: Escherichia coli

<400> SEQUENCE: 32

Gly Gln Ala Val Val Asn Ile Ser Asn Ala Ala Phe Pro Ile Leu Met
1               5                   10                  15

Ala Arg

<210> SEQ ID NO 33
<211> LENGTH: 15
<212> TYPE: PRT
<213> ORGANISM: Escherichia coli

<400> SEQUENCE: 33

Ser Ser Met Thr Val Gly Thr Asn Leu Glu Thr Val Tyr Phe Lys
1               5                   10                  15

<210> SEQ ID NO 34
<211> LENGTH: 15
<212> TYPE: PRT
<213> ORGANISM: Escherichia coli

<400> SEQUENCE: 34

Leu Thr Gln Gln Asp Val Thr Asp Leu Ile Ala Tyr Met Asn Lys
1               5                   10                  15

<210> SEQ ID NO 35
<211> LENGTH: 15
<212> TYPE: PRT
<213> ORGANISM: Escherichia coli

<400> SEQUENCE: 35

Gly Gly Ser Val Leu Ile Met Glu Asn Val Met Ser Asn Leu Lys
1               5                   10                  15

<210> SEQ ID NO 36
<211> LENGTH: 9
<212> TYPE: PRT
<213> ORGANISM: Escherichia coli

<400> SEQUENCE: 36

Glu Glu Ser Ala Ser Gly Phe Val Arg
1               5
```

<210> SEQ ID NO 37
<211> LENGTH: 13
<212> TYPE: PRT
<213> ORGANISM: Escherichia coli

<400> SEQUENCE: 37

Ser Val Val Asn Asn Asp Pro Gln Gly Tyr Pro Asp Arg
1               5                   10

<210> SEQ ID NO 38
<211> LENGTH: 13
<212> TYPE: PRT
<213> ORGANISM: Escherichia coli

<400> SEQUENCE: 38

Leu Glu Val Ala Ser Trp Gln Glu Glu Val Glu Gly Lys
1               5                   10

<210> SEQ ID NO 39
<211> LENGTH: 9
<212> TYPE: PRT
<213> ORGANISM: Escherichia coli

<400> SEQUENCE: 39

Thr Pro Glu Ser Leu Ala Ala Ala Lys
1               5

<210> SEQ ID NO 40
<211> LENGTH: 14
<212> TYPE: PRT
<213> ORGANISM: Escherichia coli

<400> SEQUENCE: 40

Ala Met Leu Gln Ala Ala Asp Leu Gly Thr Asn Ile Gln Arg
1               5                   10

<210> SEQ ID NO 41
<211> LENGTH: 13
<212> TYPE: PRT
<213> ORGANISM: Escherichia coli

<400> SEQUENCE: 41

Leu Tyr Gln His Glu Leu Tyr Phe Arg Thr Asn Gly Arg
1               5                   10

<210> SEQ ID NO 42
<211> LENGTH: 12
<212> TYPE: PRT
<213> ORGANISM: Escherichia coli

<400> SEQUENCE: 42

Gln Gly Glu Arg Leu Asn Ser Val Asp Leu Glu Arg
1               5                   10

<210> SEQ ID NO 43
<211> LENGTH: 16
<212> TYPE: PRT
<213> ORGANISM: Escherichia coli

<400> SEQUENCE: 43

Leu Tyr Gln Asn Met Ser Val Trp Leu Trp Asn Glu Thr Lys Tyr Arg
1               5                   10                  15

<210> SEQ ID NO 44

-continued

```
<211> LENGTH: 16
<212> TYPE: PRT
<213> ORGANISM: Escherichia coli

<400> SEQUENCE: 44

Lys Ser Leu Ile Asp Asn Lys Met Ile Tyr Gly Glu Glu Ser Ser Lys
1               5                   10                  15

<210> SEQ ID NO 45
<211> LENGTH: 19
<212> TYPE: PRT
<213> ORGANISM: Escherichia coli

<400> SEQUENCE: 45

Ala Gly Met Met Asn Pro Ser Tyr Pro Leu Asn Tyr Met Glu Lys Pro
1               5                   10                  15

Leu Thr Arg

<210> SEQ ID NO 46
<211> LENGTH: 20
<212> TYPE: PRT
<213> ORGANISM: Escherichia coli

<400> SEQUENCE: 46

Ser Thr Val Pro Val Thr Val Thr Val Ala Leu Ala Asp Asp Leu Thr
1               5                   10                  15

Gly Arg Glu Lys
            20

<210> SEQ ID NO 47
<211> LENGTH: 9
<212> TYPE: PRT
<213> ORGANISM: Escherichia coli

<400> SEQUENCE: 47

Thr Tyr Asp Leu Lys Ala Asn Asp Lys
1               5

<210> SEQ ID NO 48
<211> LENGTH: 13
<212> TYPE: PRT
<213> ORGANISM: Escherichia coli

<400> SEQUENCE: 48

Thr Tyr Asp Leu Lys Ala Asn Asp Lys Val Thr Phe Lys
1               5                   10

<210> SEQ ID NO 49
<211> LENGTH: 18
<212> TYPE: PRT
<213> ORGANISM: Escherichia coli

<400> SEQUENCE: 49

Val Thr Phe Lys Val Pro Tyr Gly Gly Leu Ile Tyr Ile Lys Gly Asp
1               5                   10                  15

Ser Lys

<210> SEQ ID NO 50
<211> LENGTH: 14
<212> TYPE: PRT
<213> ORGANISM: Escherichia coli

<400> SEQUENCE: 50
```

```
Ala Arg Gly Asp Glu Val Ser Asn Asp Lys Phe Gly Gly Lys
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthetic O-linked glycopeptide

<400> SEQUENCE: 51

Thr Thr Val Thr Ser Gly Gly Leu Gln Arg
1               5                   10
```

GLYCOSYLATED YGHJ POLYPEPTIDES FROM ENTEROTOXIGENIC *ESCHERICHIA COLI* (ETEC)

CROSS REFERENCE TO RELATED APPLICATIONS

This application is a divisional of and claims the benefit and priority to U.S. patent application Ser. No. 15/766,209, filed on Apr. 5, 2018, which is a U.S. National Phase application of PCT International Application Number PCT/DK2016/050321, filed on Oct. 6, 2016, designating the United States of America and published in the English language, which is an International Application of and claims the benefit of priority to European Patent Application No. 15188608.2, filed on Oct. 6, 2015. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG237-001D1.txt, the date of creation of the ASCII text file is Apr. 23, 2019, and the size of the ASCII text file is 24 KB.

TECHNICAL FIELD OF THE INVENTION

The present invention relates to a method for identifying and/or mapping of 0-linked glycoproteins. In particular, the method of the present invention includes specifically tagging the O-linked carbohydrate moieties of the glycoprotein with a label suitable for subsequent titanium dioxide enrichment and MS characterization of the glycoprotein.

BACKGROUND OF THE INVENTION

Enterotoxigenic *Escherichia coli* (ETEC) is the major source of *E. coli* mediated 30 diarrhoea in humans and livestock. ETEC infections cause more than 280 million annual episodes of diarrhoea resulting in mortality numbers exceeding 300,000 deaths of children under the age of five years.

The significant negative health- and socio-economic impact of ETEC infection manifests itself mainly in the third world nations with poor sanitation and inadequate supplies of clean water. ETEC is a diverse group of pathogens defined by their ability to colonize the small intestine and secrete heat-labile and/or heat stable enterotoxins. The complex pathogenicity is further attributed to the presence of additional bacterial virulence genes on mobile genetic elements such as plasmids and chromosomal pathogenicity islands.

Much attention has been devoted to the understanding of how ETEC and other mucosa-associated pathogens interact with host tissue during infection. Recent work has revealed that bacterial protein glycosylation plays an important role in mediating adhesion, colonization and invasion of host tissue.

Up until now, the known protein glycosylation repertoire of *E. coli* was limited to just four proteins, all of which are surface-exposed adhesins with functions in bacterial pathogenesis. The prototypical ETEC strain H10407 encodes two known glycoproteins, TibA and EtpA.

While the intimate coupling between protein glycosylation and bacterial pathophysiology has become apparent, the discovery of novel glycoproteins implicated in virulence is only advancing slowly. This gap of knowledge is linked to the inherent challenges associated with glycoproteomics. The analytical tools developed for enrichment of eukaryotic 0- and N-linked glycopeptides rely on a limited set of defined physiochemical properties, e.g. glycan hydrophilicity or specific lectin recognition, which are relatively rare in bacteria.

Discovery and characterization of glycoproteins is further complicated by heterogeneous glycosylation, low abundance and poor ionization of peptides modified with carbohydrates compared to the non-modified counterpart.

Mapping of O-linked glycan moieties has proven to be a particularly challenging 35 task owing to the diverse nature of carbohydrate structures available for protein modification in bacteria. Although methods such as periodic acid/hydrazide glycan labelling and metabolic oligosaccharide engineering (MOE) have identified glycoproteins in a range of bacteria, these techniques present limitations in the form of low specificity for glycosylated proteins and dependence on sugar uptake and integration into bacterial glycoproteins, respectively.

Although they are poorly understood, bacterial glycoproteins potentially constitute an important reservoir of novel therapeutic targets, which could be used against bacterial pathogens.

Thus, there is a great need for understanding the glycosylation patterns of proteins originating from bacteria such as ETEC, and revealing the effect of the glycosylations on for example immunogenicity.

SUMMARY OF THE INVENTION

An object of the present invention is to provide glycosylated YghJ polypeptides that are immunogenic.

In one aspect of the present invention, the polypeptide is YghJ (also known as ETEC_3241 or CBJ02741, SEQ ID NO: 1).

Another aspect of the present invention relates to the full length sequence of SEQ ID NO: 1, a polypeptide or polypeptide fragment of SEQ ID NO: 1 having at least 75% sequence identity to the full length sequence, or a B- or T-cell epitope of the full length sequence, wherein the polypeptide is glycosylated at least in one position.

Still another aspect of the present invention relates to a polypeptide comprising:
 a) SEQ ID NO: 1,
 b) a polypeptide or polypeptide fragment of SEQ ID NO: 1 having at least 75% sequence identity to SEQ ID NO: 1, or
 c) a B- or T-cell epitope of SEQ ID NO: 1,
wherein the polypeptide is glycosylated in at least one position.

Yet another aspect of the present invention relates to a polypeptide comprising:
 a) SEQ ID NO: 1,
 b) a polypeptide having at least 75% sequence identity to the full length sequence of SEQ ID NO: 1, or
 c) a polypeptide fragment of SEQ ID NO: 1 comprising at least 5 amino acids and having at least 75% sequence identity to a segment of SEQ ID NO: 1, said segment of SEQ ID NO:1 having the same number of amino acids as said polypeptide fragment,
wherein the polypeptide is glycosylated in at least one position.

A further aspect of the present invention relates to an immunogenic composition 20 comprising the polypeptide as described herein.

Yet another aspect of the present invention relates to a pharmaceutical composition comprising the polypeptide as described herein and at least one pharmaceutically acceptable carrier, excipient or diluent.

Another aspect of the present invention relates to the immunogenic composition or the pharmaceutical composition as described herein, which is a vaccine against ETEC.

A further aspect of the present invention relates to a nucleic acid sequence encoding a polypeptide as described herein.

In a further aspect of the present invention, the polypeptide, immunogenic composition, pharmaceutical composition or vaccine as described herein is for use 35 in preventing or treating infection caused by ETEC.

In another aspect of the present invention, the polypeptide, immunogenic composition, pharmaceutical composition or vaccine as described herein is for use in the preparation of a medicament for treating infection caused by ETEC.

Yet another aspect of the present invention relates to the polypeptide, immunogenic composition, pharmaceutical composition or vaccine as described herein for use in the diagnosis of an infection caused by ETEC.

A further aspect of the present invention relates to a method for immunizing a mammal, the method comprising administering to the mammal the immunogenic composition, pharmaceutical composition or vaccine as described herein.

Another aspect of the present invention relates to a method for treating a mammal, which is infected with ETEC comprising administering to the mammal the immunogenic composition, pharmaceutical composition or vaccine as described herein.

BRIEF DESCRIPTION OF THE FIGURES

The following shows β-Elimination of glycan moiety and replacement with 2-AEP through Michael addition chemistry. (1A)

Figure 2A:
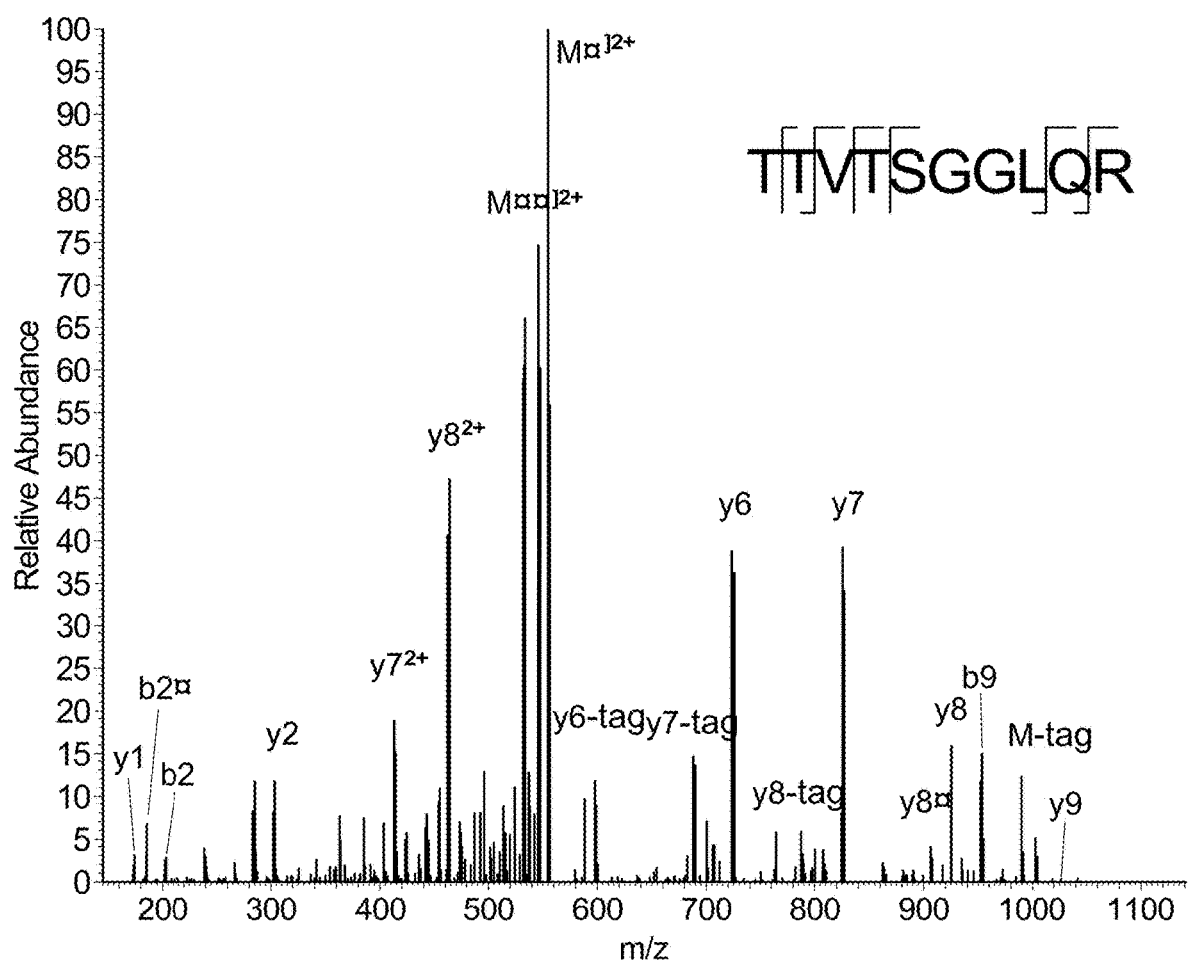
Figure 2B:
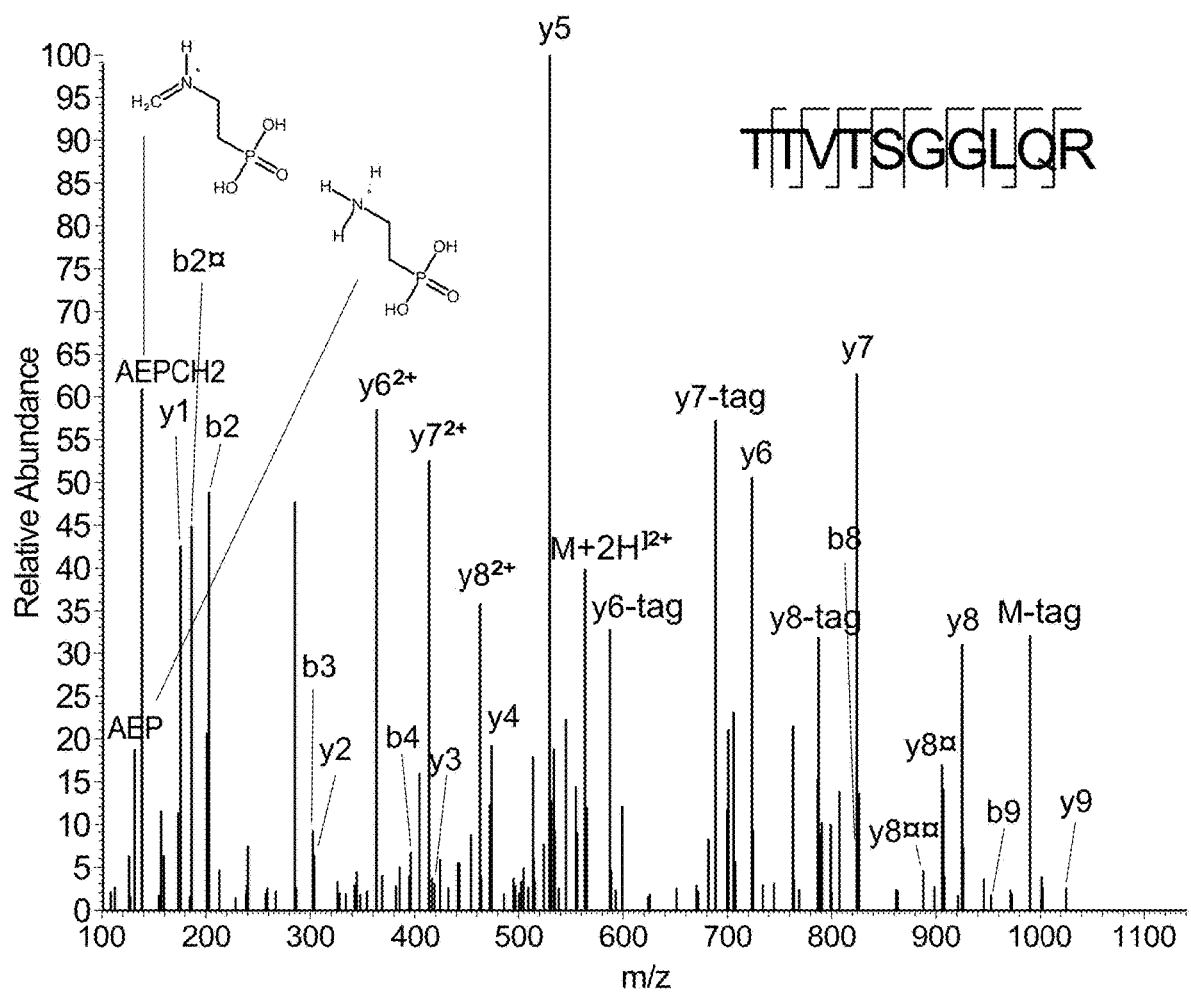

The following shows gas-phase fragmentation properties of 2-AEP tagged peptide TTVTSGGLQR (SEQ ID NO:51) with either collision-induced dissociation (CID, FIG. 2A) or the CID variant, higher-energy collisional dissociation (HCD, FIG. 2B). HCD yields a more nuanced result than CID. The AEP addition substitutes a labile glycoside bond with a stronger covalent C—N bond, which greatly improves mapping of glycosylated residues by HCD fragmentation. Moreover, HCD fragmentation yields two characteristic ions (m/z=126.03 Da and m/z=138.03 Da), useful for the identification of formerly glycosylated peptides in complex MS/MS spectra.

The present invention will now be described in more detail in the following.

DETAILED DESCRIPTION OF THE INVENTION

The present inventors have developed a novel mass spectrometry-based technique, termed BEMAP, which can be employed to map O-linked glycoproteins from theoretically any organism.

BEMAP combines a simple reaction scheme with a highly selective enrichment protocol to circumvent the challenges previously associated with bacterial glycoproteomics. The BEMAP reaction efficiently substitutes O-linked carbohydrate moieties with a 2-Aminoethyl phosphonic acid (AEP) group, which can be selectively isolated based on its affinity for titanium dioxide.

BEMAP has been employed to map novel protein glycosylation sites in ETEC strain H10407 and the non-pathogenic E. coli K-12 MG1655. Functional characterization of an H10407ΔhldE knockout strain revealed the importance of protein glycosylation for ETEC adhesion to human intestinal cells.

These results, together with other recent studies of bacterial glycoproteomes, highlight protein glycosylation in bacteria as an abundant, yet largely unexplored, posttranslational protein modification, which is central to bacterial physiology and pathophysiology.

The ETEC glycosylated proteins (polypeptides) are important in understanding the immunogenicity of ETEC. The glycosylated polypeptides disclosed herein leads to an enhanced immunogenicity compared to the same polypeptides that are not glycosylated.

The present inventors have therefore surprisingly found that certain proteins from ETEC causes an enhanced immunogenic response due to specific glycosylation of the YghJ proteins or fragments thereof.

Thus, an object of the present invention is to provide glycosylated YghJ polypeptides that are immunogenic.

Glycosylated Polypeptides

The term glycosylation refers to O-linked glycosylation. This is the attachment of a sugar molecule to a hydroxyl oxygen of either a Serine or Threonine side chain in a protein.

One such glycosylated polypeptide is YghJ (also known as ETEC_3241 or CBJ02741, SEQ ID NO: 1).

Therefore, one aspect of the present invention relates to the full length sequence of SEQ ID NO: 1, a polypeptide or polypeptide fragment of SEQ ID NO: 1 having at least 75% sequence identity to the full length sequence, or a B- or T-cell epitope of the full length sequence, wherein the polypeptide is glycosylated at least in one position. The polypeptides of the present invention may be synthetic or recombinant.

Another aspect of the present invention relates to a polypeptide comprising:
a) SEQ ID NO: 1,
b) a polypeptide or polypeptide fragment of SEQ ID NO: 1 having at least 75% sequence identity to SEQ ID NO: 1, or c) a B- or T-cell epitope of SEQ ID NO: 1,
wherein the polypeptide is glycosylated in at least one position.

Still another aspect of the present invention relates to a polypeptide comprising:
a) SEQ ID NO: 1,
b) a polypeptide having at least 75% sequence identity to the full length sequence of SEQ ID NO: 1, or
c) a polypeptide fragment of SEQ ID NO: 1 comprising at least 5 amino acids and having at least 75% sequence identity to a segment of SEQ ID NO: 1, said segment of SEQ ID NO:1 having the same number of amino acids as said polypeptide fragment,
wherein the polypeptide is glycosylated in at least one position.

The polypeptide fragments of the present invention may comprise at least 5 amino acids, such as at least 7 amino acids, at least 8 amino acids, at least 9 amino acids, at least 10 amino acids, at least 12 amino acids, at least 15 amino acids, at least 20 amino acids, at least 25 amino acids, at least 30 amino acids, at least 35 amino acids, at least 40 amino acids, at least 45 amino acids, or at least 50 amino acids.

Thus, one embodiment of the present invention relates to polypeptides as 25 described herein, wherein the polypeptide fragment comprises at least 7 amino acids, such as at least 8 amino acids, at least 9 amino acids, at least 10 amino acids, at least 12 amino acids, at least 15 amino acids, at least 20 amino acids, at least 25 amino acids, at least 30 amino acids, at least 35 amino acids, at least 40 amino acids, at least 45 amino acids, or at least 50 amino acids.

Another embodiment of the present invention relates to polypeptides as described herein, wherein the polypeptide fragment comprises at least 9 amino acids.

Still another embodiment of the present invention relates to polypeptides as described herein, wherein the polypeptide fragment comprises at least 10 amino acids.

A further embodiment of the present invention relates to polypeptides as described herein, wherein the polypeptide fragment comprises at least 20 amino acids.

The polypeptides of the present invention may be glycosylated at least in two positions, such as at least in three positions, at least four positions, at least five positions, at least six positions, seven, eight or at least nine positions.

In one embodiment of the present invention, the polypeptide is glycosylated in at least two positions.

In another embodiment of the present invention, the polypeptide is glycosylated in at least three positions.

The polypeptides can also be glycosylated in exactly one, two, three, four, five, six, seven, eight or nine positions.

Numerous examples are known in which proteins can be extensively glycosylated. Glycosylated proteins can exhibit completely different biological functions than their non-glycosylated counterparts. In the present context, a hyper-glycosylated protein (or polypeptide) is defined as an amino acid sequence being glycosylated in at least ten positions.

Thus, yet another embodiment of the present invention relates to the situation, wherein the polypeptide as described herein is hyperglycosylated.

The polypeptides of the present invention may also be characterized by certain amino acid motifs. Such motifs can be identified experimentally, by for instance BEMAP as described herein or computationally by software tools such as Motif-X, which recognizes overrepresented patterns from a sequence data set (M. F. Chou and D. Schwartz (2011).

An embodiment of the present invention consequently relates to a polypeptide as described herein, wherein the glycosylated polypeptide comprises at least one asparagine within seven amino acids from each glycosylated amino acid.

Therefore, embodiments of the present invention also encompasses glycosylated polypeptide comprising at least one asparagine within seven amino acids from each glycosylated amino acid, such as within seven, six, five, four, three, two or one amino acid from each glycosylated amino acid.

The polypeptides may also be defined by more specific amino acid motifs. A bioinformatics motif analysis of the YghJ sequence revealed several frequently occurring amino acid motifs, below presented by the specific amino acids as well as by X, which signifies an arbitrarily chosen amino acid.

```
Motif 1:  XTXNX

Motif 2:  XTXXXNX

Motif 3:  XTXXXXXXNX

Motif 4:  XTTX

Motif 5:  XSNX

Motif 6:  XSXNX

Motif 7:  XSTX

Motif 8:  XNXXXXXXSX

Motif 9:  XSXXTX

Motif 10: XSXXNX

Motif 11: XNSX

Motif 12: XXXXXXXXCSXXXXXXXXX

Motif 13: XXXXXXXXXSCXXXXXXXX

Motif 14: XXXXXXXCXSXXXXXXXXX

Motif 15: XXXXXXXXXSXCXXXXXXX

Motif 16: XXXXXXCXXSXXXXXXXXX

Motif 17: XXXXXXXXXSXXXCXXXXX

Motif 18: XXXXXCXXXSXXXXXXXXX

Motif 19: XXXXXXXXXSXXCXXXXXX

Motif 20: XXXXXXXXXSXXXXCXXXX

Motif 21: XXXXXXXXXSXXXXXCXXX

Motif 22: XXXXXXXXXTCXXXXXXXX

Motif 23: XXXXXXXXCTXXXXXXXXX

Motif 24: XXXXXXXXXTXCXXXXXXX

Motif 25: XXXXXXXCXTXXXXXXXXX

Motif 26: XXXXXXCXXTXXXXXXXXX

Motif 27: XXXXXXXXXTXXCXXXXXX

Motif 28: XXXXXXXXXTXXXCXXXXX

Motif 29: XXXXXCXXXTXXXXXXXXX

Motif 30: XXXXXXXXXTXXXXCXXXX
```

-continued

```
Motif 31: XXXXXXXXNTXXXXXXXXX

Motif 32: XXXXXXXXNXTXXXXXXXXX
```

Thus, another embodiment of the present invention relates to a polypeptide as described herein, wherein the glycosylated polypeptide comprises an amino acid motif selected from the group consisting of XTXNX, XTXXXNX, XTXXXXXXNX, XTTX, XSNX, XSXNX, XSTX, XNXXXXXXSX, XSXXTX, XSXXNX, and XNSX.

In another embodiment of the present invention relates to a polypeptide as described herein, wherein the glycosylated polypeptide comprises an amino acid motif selected from the group consisting of XXXXXXXXCSXXXXXXXXX, XXXXXXXXXSCXXXXXXXX, XXXXXXXCXSXXXXXXXXX, XXXXXXXXXSXCXXXXXXX, XXXXXXCXXSXXXXXXXXX, XXXXXXXXXSXXXCXXXXX, XXXXXCXXXSXXXXXXXXX, XXXXXXXXXSXXCXXXXXX, XXXXXXXX-SXXXXCXXXX, XXXXXXXXXSXXXXXCXXX, XXXXXXXXXTCXXXXXXXX, XXXXXXXX-CTXXXXXXXXX, XXXXXXXXXTXCXXXXXXX, XXXXXXXCXTXXXXXXXXX, XXXXXXCXX-TXXXXXXXXX, XXXXXXXXXTXXCXXXXXX, XXXXXXXXXTXXXCXXXXX, XXXXXCXXX-TXXXXXXXXX, XXXXXXXXXTXXXXCXXXX, XXXXXXXXNTXXXXXXXXX and XXXXXXXNX-TXXXXXXXXX.

In a further embodiment of the present invention relates to a polypeptide as described herein, wherein the glycosylated polypeptide comprises an amino acid motif selected from the group consisting of XTXNX, XTXXXNX, XTXXXXXXNX, XTTX, XSNX, XSXNX, XSTX, XNXXXXXXSX, XSXXTX, XSXXNX, XNSX, XXXXXXXXCSXXXXXXXXX, XXXXXXXXX-SCXXXXXXXX, XXXXXXXCXSXXXXXXXXX, XXXXXXXXXSXCXXXXXXX, XXXXXXCXX-SXXXXXXXXX, XXXXXXXXXSXXCXXXXX, XXXXXCXXXSXXXXXXXXX, XXXXXXXXXSXX-CXXXXXX, XXXXXXXXXSXXXXCXXXX, XXXXXXXXXSXXXXXCXXX, XXXXXXXXX-TCXXXXXXXX, XXXXXXXXCTXXXXXXXXX, XXXXXXXXXTXCXXXXXXX, XXXXXXXCX-TXXXXXXXXX, XXXXXXCXXTXXXXXXXXX, XXXXXXXXXTXXCXXXXXX, XXXXXXXXXTXXX-CXXXXX, XXXXXCXXXTXXXXXXXXX, XXXXXXXXXTXXXXCXXXX, XXXXXXXX-NTXXXXXXXXX and XXXXXXXNXTXXXXXXXXX.

Sequence Identity

Glycosylated polypeptides may be obtained directly from a bacterial culture by purification or they can be chemically synthesized.

In an embodiment of the present invention, the polypeptide originates from Enterotoxigenic *Escherichia coli* (ETEC). Examples of such polypeptides are given in the present disclosure.

The polypeptides can also be functional variants of the polypeptides disclosed herein. Such variance can be determined by sequence identity.

The term "sequence identity" indicates a quantitative measure of the degree of homology between two amino acid sequences of substantially equal length or between two nucleic acid sequences of substantially equal length. The two sequences to be compared must be aligned to best possible fit with the insertion of gaps or alternatively, truncation at the ends of the protein sequences. The sequence identity can be calculated as $(N_{ref}-N_{dif})100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (W. R Pearson and D. J. Lipman (1988)). In one embodiment of the invention, alignment is performed with the sequence alignment method ClustalW with default parameters as described by J. D. Thompson et al (1994).

For calculations of sequence identity when comparing polypeptide fragments with longer amino acid sequences, the polypeptide fragment is aligned with a segment of the longer amino acid sequence. The polypeptide fragment and the segment of the longer amino acid sequence may be of substantially equal length. Thus, the polypeptide fragment and the segment of the longer amino acid sequence may be of equal length. After alignment of the polypeptide fragment with the segment of the longer amino acid sequence, the sequence identity is computed as described above.

A preferred minimum percentage of sequence identity is at least 75%, such as at least 80%, such as at least 85%, at least 90%, at least 91%, at least 92%, at least 93%, at least 94%, at least 95%, at least 96%, at least 97%, at least 98%, at least 99%, and at least 99.5%.

Thus, one embodiment of the present invention relates to a polypeptide as described herein, wherein the polypeptide or polypeptide fragment has at least 80% sequence identity to the full-length sequence of SEQ ID No: 1, such as at least 80%, such as at least 85%, at least 90%, at least 91%, at least 92%, at least 93%, at least 94%, at least 95%, at least 96%, at least 97%, at least 98%, at least 99%, or at least 99.5%.

An embodiment of the present invention relates to a polypeptide as described herein, wherein the polypeptide or polypeptide fragment has at least 90% sequence identity to SEQ ID NO: 1.

Another embodiment of the present invention relates to a polypeptide as described herein, wherein the polypeptide has at least 90% sequence identity to the full length sequence of SEQ ID NO: 1, and the polypeptide fragment has at least 90% sequence identity to a segment of SEQ ID NO: 1, said segment of SEQ ID NO:1 having the same number of amino acids as said polypeptide fragment.

Preferably, the numbers of substitutions, insertions, additions or deletions of one or more amino acid residues in the polypeptide is limited, i.e. no more than 1, 2, 3, 4, 5, 6, 7, 8, 9, 10 substitutions, no more than 1, 2, 3, 4, 5, 6, 7, 8, 9, 10 insertions, no more than 1, 2, 3, 4, 5, 6, 7, 8, 9, 10 additions, and no more than 1, 2, 3, 4, 5, 6, 7, 8, 9, 10 deletions compared to the immunogenic polypeptide units based on polypeptides disclosed herein.

B- or T-Cell Epitopes

Polypeptides such as the ETEC proteins disclosed herein can contain immunogenic parts, such as B- or T-cell epitopes.

The immunogenic part of an immunogenic polypeptide is the part of the polypeptide, which elicits an immune response in an animal or a human being, and/or in a biological sample determined by any of the biological assays known to the skilled person working with immune responses.

The immunogenic part of a polypeptide may be a T-cell epitope or a B-cell epitope and can be related to one or a few relatively small parts of the polypeptide, they can be scattered throughout the polypeptide sequence or be situated in specific parts of the polypeptide.

In order to identify relevant T-cell epitopes which are recognized during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to assays known to the skilled person working with immune responses.

Another method utilizes overlapping oligopeptides for the detection of MHC class II epitopes, preferably synthetic, having a length of e.g. 20 amino acid residues derived from the polypeptide. These peptides can be tested in biological assays and some of these will give a positive response (and thereby be immunogenic) as evidence for the presence of a T cell epitope in the peptide.

For the detection of MHC class I epitopes it is possible to predict peptides that will bind and hereafter produce these peptides synthetically and test them in relevant biological assays. The peptides preferably having a length of e.g. 8 to 20 amino 35 acid residues derived from the polypeptide. B-cell epitopes can be determined by analyzing the B-cell recognition to overlapping peptides covering the polypeptide of interest.

B-cell epitopes differ from T-cell epitopes in that they are conformational epitopes that require a three dimensional structure in order to raise an immune response. Without being bound by theory, variants of B-cell epitopes can be identified through key amino acids (for example glycosylated amino acids) and a certain length of the polypeptide while remaining immunogenic.

Thus, an embodiment of the present invention therefore relates to epitopes, such as B- or T-cell epitopes of the polypeptides mentioned herein.

A common feature of the polypeptides of the present invention is their capability to induce an immunological response as illustrated in the examples. It is understood that within the scope of the present invention are variants of the polypeptides of the invention produced by substitution, insertion, addition or deletion while remaining immunogenic.

Examples of such epitopes are listed in the examples of the present disclosure and include SEQ ID NOs: 2-23. Other examples include SEQ ID NOs: 24-50. Also polypeptides with a minimum percentage of sequence identity to any of SEQ ID NOs: 2-50 form part of the invention.

A preferred minimum percentage of sequence identity to any of SEQ ID NOs: 2-50 is at least 75%, such as at least 80%, such as at least 85%, at least 90%, at least 91%, at least 92%, at least 93%, at least 94%, at least 95%, at least 96%, at least 97%, at least 98%, at least 99%, and at least 99.5%.

Therefore, an embodiment of the present invention relates to a polypeptide as 30 described herein, wherein the polypeptide has at least 75% sequence identity to the full-length sequence of SEQ ID NOs: 2-50, such as at least 80%, such as at least 85%, at least 90%, at least 91%, at least 92%, at least 93%, at least 94%, at least 95%, at least 96%, at least 97%, at least 98%, at least 99%, or at least 99.5%.

Thus, an embodiment of the present invention relates to a polypeptide as described herein, wherein the glycosylated polypeptide is selected from the group of glycosylated polypeptides consisting of SEQ ID NOs: 2-50 and polypeptides having at least 75% sequence identity to the full length sequence of SEQ ID Nos: 2-50.

Another embodiment of the present invention relates to a polypeptide as described herein, wherein the glycosylated polypeptide is selected from the group of glycosylated polypeptides consisting of SEQ ID NOs: 2-23 and polypeptides having at least 75% sequence identity to the full length sequence of SEQ ID Nos: 2-23.

Yet another embodiment of the present invention relates to a polypeptide as described herein, wherein the glycosylated polypeptide is selected from the group of glycosylated polypeptides consisting of SEQ ID NOs: 24-50 and polypeptides having at least 75% sequence identity to the full length sequence of SEQ ID Nos: 24-50.

A further embodiment of the present invention relates to a polypeptide as described herein, wherein the glycosylated polypeptide has at least 90% sequence identity to the full length sequence of SEQ ID Nos: 2-50.

An even further embodiment of the present invention relates to a polypeptide as described herein, wherein the glycosylated polypeptide has at least 90% sequence identity to the full length sequence of SEQ ID Nos: 2-23.

Still another embodiment of the present invention relates to a polypeptide as described herein, wherein the glycosylated polypeptide has at least 90% sequence identity to the full length sequence of SEQ ID Nos: 24-50.

The polypeptides may also be given by a specific sequence selected from SEQ ID Nos: 2-50.

Therefore, an embodiment of the present invention relates to a polypeptide as described herein, wherein the glycosylated polypeptide is selected from the group of glycosylated polypeptides consisting of SEQ ID NOs: 2-50.

Thus, in one embodiment of the present invention, the glycosylated polypeptide is selected from the group of glycosylated polypeptides consisting of SEQ ID NOs: 2-23.

Another embodiment of the present invention relates to a polypeptide as described herein, wherein the glycosylated polypeptide is selected from the group of glycosylated polypeptides consisting of SEQ ID NOs: 24-50.

Key features of these epitopes or fragments are that they comprise one or more glycosylations at central positions.

Polypeptide Purity

In the present context the term "substantially pure polypeptide" means a polypeptide preparation which contains at most 5% by weight of other polypeptide material with which it is associated natively or during recombinant or synthetic production (lower percentages of other polypeptide material are preferred, e.g. at most 4%, at most 3%, at most 2%, at most 1%, and at most ½%).

It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide is in "essentially pure form", i.e. that the polypeptide is essentially free of any other antigen with which it is natively associated, i.e. free of any other antigen from bacteria. This can be accomplished by preparing the polypeptide by means of recombinant methods in a host cell, or by synthesizing the polypeptide by the well-known methods of solid or liquid phase peptide synthesis, and by using appropriate purification procedures well known to the person of ordinary skill in the art.

Thus in one embodiment of the present invention are the polypeptides of the present invention substantially pure or in essentially pure form.

Fusion Polypeptides

Two or more of the polypeptides disclosed herein may be fused to form fusion polypeptides.

Therefore, an embodiment of the present invention relates to a situation wherein the polypeptide is a fusion polypeptide.

The polypeptides to which fusion is made may originate from ETEC or alternatively be other polypeptides that are beneficial when an enhanced immune response against ETEC is required.

Thus, another embodiment of the present invention relates to a polypeptide as described herein, wherein the polypeptide is fused to a polypeptide originating from ETEC.

Yet another embodiment of the present invention relates to a polypeptide as described herein, wherein the polypeptide is a fusion polypeptide, said fusion polypeptide comprising one or more glycosylated polypeptide selected from the group of glycosylated polypeptides consisting of SEQ ID NOs: 2-50.

A further embodiment of the present invention relates to a polypeptide as 25 described herein, wherein the polypeptide is a fusion polypeptide, said fusion polypeptide comprising one or more glycosylated polypeptide selected from the group of glycosylated polypeptides consisting of SEQ ID NOs: 2-23.

An even further embodiment of the present invention relates to a polypeptide as 30 described herein, wherein the polypeptide is a fusion polypeptide, said fusion polypeptide comprising one or more glycosylated polypeptide selected from the group of glycosylated polypeptides consisting of SEQ ID NOs: 24-50.

Another embodiment of the present invention relates to a polypeptide as 35 described herein, wherein the polypeptide is a fusion polypeptide, said fusion polypeptide consisting of two or more glycosylated polypeptides selected from the group of glycosylated polypeptides consisting of SEQ ID NOs: 2-50.

Another embodiment of the present invention relates to a polypeptide as described herein, wherein the polypeptide is a fusion polypeptide, said fusion polypeptide consisting of two or more glycosylated polypeptides selected from the group of glycosylated polypeptides consisting of SEQ ID NOs: 2-23.

Another embodiment of the present invention relates to a polypeptide as described herein, wherein the polypeptide is a fusion polypeptide, said fusion polypeptide consisting of two or more glycosylated polypeptides selected from the group of glycosylated polypeptides consisting of SEQ ID NOs: 24-50.

Immunogenicity

An immunogenic polypeptide is defined as a polypeptide that induces an immune response. The immune response may be monitored by one of the following methods:

An in vitro cellular response is determined by release of a relevant cytokine such as IFN-γ, from lymphocytes withdrawn from an animal or human currently or previously infected with ETEC, or by detection of proliferation of these T cells. The induction is performed by addition of the polypeptide or the immunogenic part to a suspension comprising from $1 \times 10^5$ cells to $3 \times 10^5$ cells per well. The cells are isolated from either blood, the spleen, the liver or the lung and the addition of the polypeptide or the immunogenic part of the polypeptide result in a concentration of not more than 20 µg per ml suspension and the stimulation is performed from two to five days. For monitoring cell proliferation, the cells are pulsed with radioactive labeled Thymidine and after 16-22 hours of incubation, the proliferation is detected by liquid scintillation counting. A positive response is a response more than background plus two standard deviations. The release of IFN-γ can be determined by the ELISA method, which is well known to a person skilled in the art. A positive response is a response more than background plus two standard deviations. Other cytokines than IFN-γ could be relevant when monitoring an immunological response to the polypeptide, such as IL-12, TNF-α, IL-4, IL-5, IL-10, IL-6, TGF-β.

Another and more sensitive method for determining the presence of a cytokine (e.g. IFN-γ) is the ELISPOT method where the cells isolated from either the blood, the spleen, the liver or the lung are diluted to a concentration of preferable of 1 to $4 \times 10^6$ cells/ml and incubated for 18-22 hrs in the presence of the polypeptide or the immunogenic part of the polypeptide resulting in a concentration of not more than 20 µg per ml. The cell suspensions are hereafter diluted to 1 to $2 \times 10^6$/ml and transferred to Maxisorp plates coated with anti-IFN-γ and incubated for preferably 4 to 16 hours. The IFN-γ producing cells are determined by the use of labelled secondary anti-IFN-antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or an ETEC infected person where the T cell lines have been driven with either live ETEC, extracts from the bacterial cell or culture filtrate for 10 to 20 days with the addition of IL-2. The induction is performed by addition of not more than 20 µg polypeptide per ml suspension to the T cell lines containing from $1 \times 10^5$ cells to $3 \times 10^5$ cells per well and incubation is performed from two to six days. The induction of IFN-γ or release of another relevant cytokine is detected by ELISA. The stimulation of T cells can also be monitored by detecting cell proliferation using radioactively labeled Thymidine as described above. For both assays, a positive response is a response more than background plus two standard deviations.

An in vivo cellular response may be determined as a positive DTH response after intradermal injection or local application patch of at most 100 µg of the polypeptide or the immunogenic part to an individual who is clinically or subclinically infected with ETEC, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic part is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the presence or absence of a specific label e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of an ETEC. Readout for induced protection could be decrease of the bacterial load in target organs compared to non-vaccinated animals, prolonged survival times compared to non-vaccinated animals and diminished weight loss or pathology compared to non-vaccinated animals.

Thus, the glycosylated polypeptides described herein are immunogenic when one of the above-described tests is positive.

In one aspect of the present invention are the polypeptides described herein immunogenic.

Such an immunogenic polypeptide may be used for immunizing a subject to infectious bacteria. Thus, an embodiment of the present invention relates to a polypeptide as described herein for use in immunizing a mammal against ETEC.

Another embodiment of the present invention relates to a polypeptide as described herein for use in immunizing a human against ETEC.

Another aspect of the present invention relates to a composition comprising a polypeptide as described herein. Such composition will constitute an immunogenic composition.

Antibodies

The glycosylated polypeptides disclosed herein can constitute epitopes.

An epitope, also known as antigenic determinant, is the part of an antigen that is recognized by the immune system, specifically by antibodies, B cells, or T cells.

The epitopes of protein antigens are divided into two categories, conformational epitopes and linear epitopes, based on their structure and interaction with the paratope.

A conformational epitope is composed of discontinuous sections of the antigen's amino acid sequence.

These epitopes interact with the paratope based on the 3-D surface features and shape or tertiary structure of the antigen.

By contrast, linear epitopes interact with the paratope based on their primary structure. A linear epitope is formed by a continuous sequence of amino acids from the antigen.

Thus, one aspect of the present invention relates to an antibody that binds to an epitope described herein.

Antibodies raised against the epitope may be either polyclonal or monoclonal.

The antibodies may be suitable to generate chimeric and/or human versions that could be appropriate for human in vivo use.

Thus, the invention is also concerned with the polypeptides as described herein for use in animals to produce antisera for diagnostic and therapeutic purposes.

Antibodies obtained from animals exposed to the polypeptides as described herein, may be used for the treatment or diagnosis of a bacterial infection, such as an ETEC infection.

The immunoglobulin heavy chain (IgH) is the large polypeptide subunit of an antibody (immunoglobulin). A typical antibody is composed of two immunoglobulin (Ig) heavy chains and two Ig light chains.

Several different types of heavy chain exist that define the class or isotype of an antibody. These heavy chain types vary between different animals.

The immunoglobulin light chain is the small polypeptide subunit of an antibody (immunoglobulin).

There are two types of light chain in humans (as in other mammals), kappa (κ) chain, encoded by the immunoglobulin kappa locus on chromosome 2 and the lambda (λ) chain, encoded by the immunoglobulin lambda locus on chromosome 22.

Antibodies are produced by B lymphocytes, each expressing only one class of light chain.

Once set, light chain class remains fixed for the life of the B lymphocyte.

In a healthy individual, the total kappa to lambda ratio is roughly 2:1 in serum (measuring intact whole antibodies) or 1:1.5 if measuring free light chains, with a highly divergent ratio indicative of neoplasm.

The exact normal ratio of kappa to lambda ranges from 0.26 to 1.65.

Both the kappa and the lambda chains can increase proportionately, maintaining a normal ratio.

Carriers, Excipients and Diluents

Pharmaceutical compositions comprising the polypeptides described herein may be administered in a physiologically acceptable medium (e.g., deionized water, phosphate buffered saline (PBS), saline, aqueous ethanol or other alcohol, plasma, proteinaceous solutions, mannitol, aqueous glucose, vegetable oil, or the like).

Thus, an embodiment of the present invention relates to a composition comprising a polypeptide as described herein that constitutes a pharmaceutical composition.

Buffers may also be included, particularly where the media are generally buffered at a pH in the range of about 5 to 10, where the buffer will generally range in concentration from about 50 to 250 mM salt, where the concentration of salt will generally range from about 5 to 500 mM, physiologically acceptable stabilizers, and the like.

The compounds may be lyophilized for convenient storage and transport.

Thus, in a further embodiment of the present invention the composition comprises one or more excipients, diluents and/or carriers.

Aqueous suspensions may contain the active materials in admixture with excipients suitable for the manufacture of aqueous suspensions.

Such excipients include suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

Thus, an aspect of the present invention relates to a pharmaceutical composition comprising a polypeptide as described herein and at least one pharmaceutically acceptable carrier, excipient or diluent.

Vaccines, Treatment and Administration

The polypeptides, immunogenic compositions, and pharmaceutical composition may constitute a vaccine against ETEC.

Therefore, an aspect of the present invention relates to an immunogenic composition or a pharmaceutical composition as defined herein, which is a vaccine against ETEC.

An embodiment of the present invention relates to a polypeptide as described herein for use in a vaccine against ETEC. Such a vaccine may be for use in a mammal, preferably a human.

Another embodiment of the present invention relates to a polypeptide as described herein for use in the preparation of a vaccine against ETEC. Such a vaccine may be for use in a mammal, preferably a human.

Key features of vaccines is that they are recognized by the recipient's immune response, generate a response, and ultimately decrease the bacterial load of ETEC.

The vaccines are administered in a manner compatible with the dosage formulation, and in such amount as will be prophylactic or therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms of the fusion polypeptide of the invention per vaccination with a preferred range from about 0.1 µg to 1000 µg, such as in the range from about 1 µg to 300 µg, and especially in the range from about 10 µg to 100 µg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral, nasal or mucosal application in either a solid form containing the active ingredients (such as a pill, suppository or capsule) or in a physiologically acceptable dispersion, such as a spray, powder or liquid, or parenterally, by injection, for example, subcutaneously, intradermally or intramuscularly or transdermally applied. The dosage of the vaccine will depend on the route of administration and will vary according to the age of the person to be vaccinated and, to a lesser degree, the size of the person to be vaccinated. Currently, most vaccines are administered intramuscularly by needle injection and this is likely to continue as the standard route. However, vaccine formulations that induce mucosal immunity have been developed, typically by oral or nasal delivery. One of the most widely studied delivery systems for induction of mucosal immunity contains cholera toxin (CT) or its B subunit. This protein enhances mucosal immune responses and induces IgA production when administered in vaccine formulations. An advantage is the ease of delivery of oral or nasal vaccines. Modified toxins from other microbial species, which have reduced toxicity but retained immunostimulatory capacity, such as modified heat-labile toxin from Gram-negative bacteria or staphylococcal enterotoxins may also be used to generate a similar effect. These molecules are particularly suited to mucosal administration.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

Thus, an aspect of the present invention relates to an immunogenic composition, a pharmaceutical composition, or a vaccine as described herein, which is formulated for intradermal, transdermal, subcutaneous, intramuscular or mucosal application.

The adjuvant is preferably selected from the group consisting of dimethyloctadecylammonium bromide (DDA), dimethyloctadecenylammonium bromide (DODAC), Quil A, poly I:C, aluminium hydroxide, Freund's incomplete adjuvant, IFN-γ, IL-2, IL-12, monophosphoryl lipid A (MPL), Treholose Dimycolate (TDM), Trehalose Dibehenate and muramyl dipeptide (MDP).

The polypeptides may also be used for immunizing a mammal against ETEC or treating the mammal against ETEC.

Therefore, one aspect of the present invention relates to a method for immunizing a mammal, the method comprising administering to the mammal an immunogenic composition, a pharmaceutical composition or a vaccine as described herein.

Another aspect of the present invention relates to a method for treating a mammal, which is infected with ETEC comprising administering to the mammal an immunogenic composition, a pharmaceutical composition or a vaccine as described herein.

An embodiment of the present invention relates to a polypeptide, an immunogenic composition or a pharmaceutical composition for use as described herein or a method as described herein, wherein the mammal is a human.

In another embodiment of the present invention is the mammal an animal selected from the group consisting of a pig, a cow, a sheep, and a horse.

A further aspect of the present invention relates to a polypeptide, an immunogenic composition, a pharmaceutical composition, or a vaccine as described herein for use in preventing or treating infection caused by ETEC.

Yet another aspect of the present invention relates to a polypeptide, an immunogenic composition, a pharmaceutical, or a vaccine as described herein for use in the preparation of a medicament for treating infection caused by ETEC.

Nucleic Acids

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least one epitope is preferably used, having a length from about 18 to about 1000 nucleotides, the molecule being optionally inserted into a vector.

When the nucleic acid molecule is used as a probe, as a primer or in antisense therapy, a molecule having a length of 10-100 is preferably used.

According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives).

Thus, one aspect of the present invention relates to a nucleic acid sequence encoding a polypeptide as described herein.

Diagnosis

Immunodiagnostics are well suited for the detection of even the smallest of amounts of biochemical substances such as antibodies. Antibodies specific for a desired antigen can be conjugated with a radiolabel, fluorescent label, or color-forming enzyme and are used as a "probe" to detect it. Well known applications include pregnancy tests, immunoblotting, ELISA and immunohistochemical staining of microscope slides. The speed, accuracy and simplicity of such tests has led to the development of rapid techniques for the diagnosis of disease.

Therefore, an aspect of the present invention relates to a polypeptide, an immunogenic composition, a pharmaceutical composition, or a vaccine as described herein for use in the diagnosis of an infection caused by ETEC.

The polypeptide, immunogenic composition, or pharmaceutical composition as described herein may also be used to detect the presence of ETEC in a sample or used as an indication whether a sample or subject may contain ETEC.

It should be noted that embodiments and features described in the context of one of the aspects of the present invention also apply to the other aspects of the invention.

All patent and non-patent references cited in the present application, are hereby incorporated by reference in their entirety.

Items

The invention will now be described in further details in the following non-limiting examples.

EXAMPLES

Example 1—BEMAP Method Results

BEMAP relies on β-elimination of O-linked carbohydrate modifications, Michael addition of 2-Aminoethyl phosphonic acid (AEP) and $TiO_2$ enrichment of phosphopeptides. Thus, BEMAP combines a firmly established in vitro chemical modification with a highly selective enrichment protocol (Thingholm et al., 2006) and the reactions take place in a single volume without the need for intermediate purification steps as described in the Experimental Procedures section.

Figure 1A:
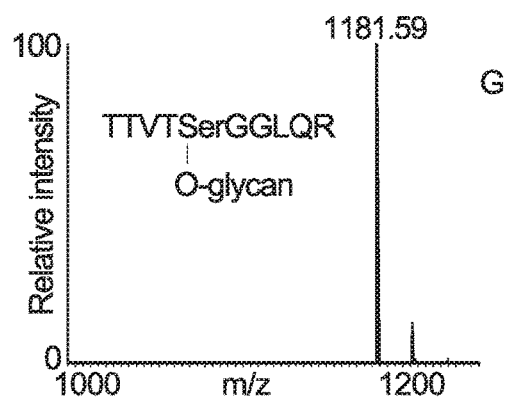
FIG. 1A shows MALDI MS spectrum of TTVTSGGLQR (SEQ ID NO:51) (m/z=1181.59 Da) synthetic O-linked glycopeptide. (1B) The FIG. 1B shows that the BEMAP reaction efficiently replaces the carbohydrate moiety with the 2-AEP molecule and produces a phosphopeptide with the mass of 1126.64 Da. Minor traces of beta-eliminated as well as intact peptide can be observed (m/z=1001.62 Da and 1181.59, respectively). (1C) The FIG. 1C shows that the AEP modified peptide is selectively enriched with TiO$_2$ as both the glycopeptide and the beta-eliminated peptide is absent in the MALDI MS spectrum. (1D)
Figure 1D:
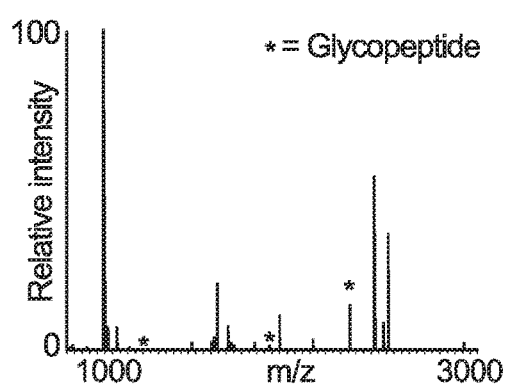
FIG. 1D shows a MALDI MS peptide mass fingerprint of a Tryptic digest of heptosylated protein Ag43. Ag43 can be digested into a mixture of heptosylated as well as unmodified peptides. Peptides marked with an asterisk indicate heptosylation. (1E)
Figure 1B:
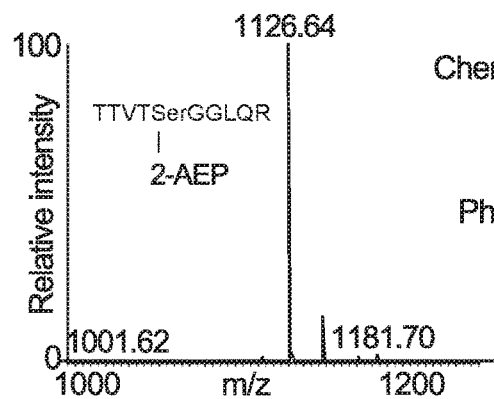
FIG. 1E shows that BEMAP converts heptosylated peptides into phosphopeptides; modified peptides are indicated. (1F) Specific
FIG. 1F shows TiO$_2$ enrichment of phosphopeptides.

The BEMAP method was first established using a synthetic mannosylated peptide as a model compound. As shown in FIGS. 1A and 1B, MALDI MS demonstrated that BEMAP efficiently replaces the carbohydrate moiety of the synthetic peptide (m/z=1181.59 Da) with the AEP group and thus produces a phosphopeptide (m/z=1126.64 Da).

Figure 1E:
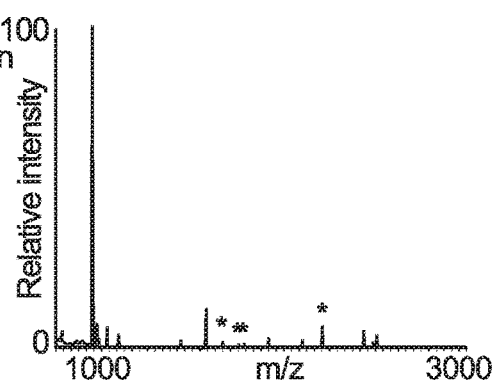
Figure 1C:
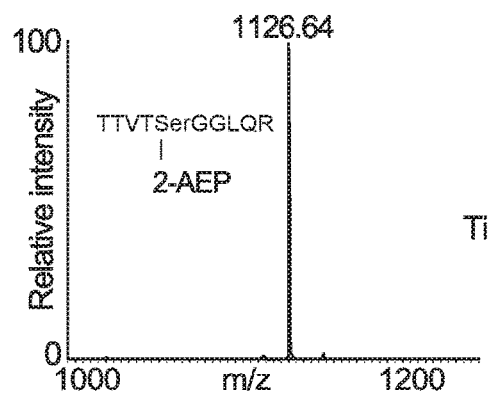

The overall efficiency of substitution exceeds 95% (FIG. 1B) without the formation of degradation products. The AEP-modified peptide was then strongly enriched using affinity chromatography with $TiO_2$; both the intact glycopeptide and the β-eliminated peptide (1001.62 Da) were absent in the MALDI MS spectrum after enrichment (FIG. 1C).

The inventors found that BEMAP converts other glycopeptides into a phosphopeptide, independent of the identity of the linked monosaccharide (data not shown). It should be noted that the $TiO_2$ purification step of BEMAP also targets phosphopeptides. Therefore, as a precaution the inventors use the enzyme Alkaline phosphatase to dephosphorylate any native phosphopeptides which otherwise may result in false positive identifications.

The inventors analyzed the gas phase-induced fragmentation properties of the converted glycopeptide. As shown in FIG. 2, the exchange of a carbohydrate moiety with AEP has several advantages. The AEP addition substitutes a labile glycoside bond with a stronger covalent C—N bond, which greatly improves mapping of glycosylated residues by higher-energy collisional dissociation (HCD) fragmentation. Moreover, the AEP group yielded two characteristic ions during HCD fragmentation (m/z=126.03 Da and m/z=138.03 Da), which are very useful for the identification of formerly glycosylated peptides in complex MS/MS spectra. It should be noted that the AEP molecule is constituted by a phosphonate functional group, which is stable under CID and HCD fragmentation conditions compared to the phosphate one, which is labile under these conditions. This allows unambiguous assignment of modified amino acid residues and avoids false positives in site localization assignment (data not shown).

Figure 1F:
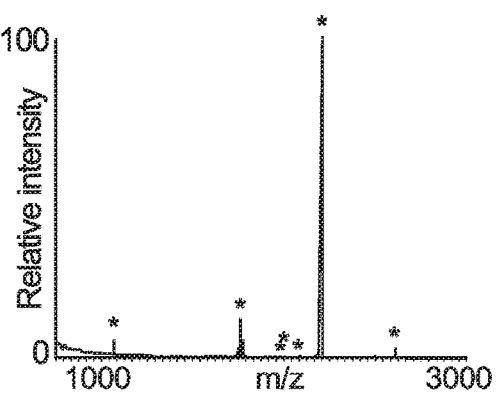

Next, the inventors applied BEMAP to a purified heptosylated protein: Ag43 from *E. coli* (Knudsen et al., 2008). As may be seen in FIG. 1D, in-gel digestion of the glycosylated protein yielded heptosylated and unmodified peptides. Heptosylated peptides are marked by an asterisk. From the digested peptide mix, BEMAP enriched the three heptosylated peptides present in FIG. 1D as well as four additional glycopeptides initially undetectable by MALDI MS (FIGS. 1E and 1F). It is concluded that BEMAP is a specific and sensitive method for detecting protein glycosylation.

Results

The outer membrane protein fraction of H10407 was isolated and subjected to BEMAP analysis for identification of glycoproteins. This approach identified the protein YghJ, a putative lipoprotein AcfD homolog.

DISCUSSION

BEMAP relies on nucleophile tagging using 2-Aminoethyl phosphonic acid (AEP) rather than e.g. DTT. BEMAP method selectivity is achieved with the glycan-for-phosphate molecule exchange combined with a highly specific enrichment protocol for downstream sample processing (Thingholm et al., 2006). Importantly, the BEMAP chemistry can be applied in principle to any organism on a large-scale proteomics level irrespective of the chemical properties of the O-linked monosaccharide. As demonstrated in FIG. 1, BEMAP replaces the carbohydrate moiety of a synthetic glycosylated peptide with a phosphotag in a chemical reaction exceeding 95% efficiency. Moreover, HCD MS/MS fragmentation of enriched BEMAP samples yields diagnostic ions instrumental for glycopeptide MS/MS spectrum identification as well as enabling unambiguous assignment of the modified amino acid residue, see FIG. 2.

To identify specific pathogenic *E. coli* associated glycoproteins of potential therapeutic value the inventors compared the outer membrane protein complement to non-pathogenic reference strain MG1655 sampled under identical conditions. By applying the BEMAP workflow, the inventors identified the ETEC vaccine candidate YghJ, a putative lipoprotein AcfD homolog. Based on analyses, the inventors propose that novel vaccines directed against ETEC should not only be selected amongst the glycoproteins expressed by the pathogen but can in principle also be targeting glycosylated domains of proteins which otherwise share 100% identity among *E. coli* strains.

Experimental Procedures

Lyophilized peptide sample is resuspended in 100 µl BEMAP solution consisting of 0.4 M 2-AEP (Sigma;

268674), 0.75 M NaOH (Sigma; S8045), 20 mM Ba(OH)$_2$ (Sigma; 433373) and incubate at 37° C. in a heating block for 3.15 hours shaking at 1300 r.p.m. The reaction is stopped by acidification (1% TFA final concentration). Sample volume is increased to 1 ml and the peptides are purified on an Oasis® HLB Plus short cartridge (Waters) as recommend by manufacturer and subsequently lyophilized. TiO$_2$ enrichment was performed as described by Tingholm et al., 2006.

ETEC H10407 lead molecule: Putative lipoprotein AcfD homolog YghJ, ETEC_3241, CBJ02741

```
Primary sequence of YghJ (SEQ ID NO: 1):
MNKKFKYKKS LLAAILSATL LAGCDGGGSG SSSDTPPVDS

GTGSLPEVKP DPTPNPEPTP EPTPDPEPTP EPIPDPEPTP

EPEPEPVPTK TGYLTLGGSQ RVTGATCNGE SSDGFTFKPG

EDVTCVAGNT TIATFNTQSE AARSLRAVEK VSFSLEDAQE

LAGSDDKKSN VSLVTSSNS CPANTEQVCL TFSSVIESKR

FDSLYKQIDL APEEFKKLVN EEVENNAATD KAPSTHTSPV

VPVTTPGTKP DLNASFVSAN AEQFYQYQPT EIILSEGRLV

DSQGYGVAGV YYTNSGRGV TGENGEFSFS WGEAISFGID

TFELGSVRGN KSTIALTELG DEVRGANIDQ LIHRYSTTGQ

NNTRVVPDDV RKVFAEYPNV INEIINLSLS NGATLGEGEQ

VVNLPNEFIE QFNTGQAKEI DTAICAKTDG CNEARWFSLT

TRNVNDGQIQ GVINKLWGVD TNYKSVSKFH VFHDSTNFYG

STGNARGQAV VNISNAAFPI LMARNDKNYW LAFGEKRAWD

KNELAYITEA PSIVRPENVT RETASFNLPF ISLGQVGDGK

LMVIGNPHYN SILRCPNGYS WNGGVNKDGQ CTLNSDPDDM

KNFMENVLRY LSNDRWLPDA KSSMTVGTNL ETVYFKKHGQ

VLGNSAPFAF HKDFTGITVK PMTSYGNLNP DEVPLLILNG

FEYVTQWGSD PYSIPLRADT SKPKLTQQDV TDLIAYMNKG

GSVLIMENVM SNLKEESASG FVRLLDAAGL SMALNKSVVN

NDPQGYPDRV RQRRSTPIWV YERYPAVDGK PPYTIDDTTK

EVIWKYQQEN KPDDKPKLEV ASWQEEVEGK QVTQFAFIDE

ADHKTPESLA AAKQRILDAF PGLEVCKDSD YHYEVNCLEY

RPGTDVPVTG GMYVPQYTQL DLSADTAKAM LQAADLGTNI

QRLYQHELYF RTNGRQGERL NSVDLERLYQ NMSVWLWNET

KYRYEEGKED ELGFKTFTEF LNCYTNNAYV GTQCSAELKK

SLIDNKMIYG EESSKAGMMN PSYPLNYMEK PLTRLMLGRS

WWDLNIKVDV EKYPGVVNTN GETVTQNINL YSAPTKWFAG

NMQSTGLWAP AQQEVSIESK STVPVTVTVA LADDLTGREK

HEVSLNRPPR VTKTYDLKAN DKVTFKVPYG GLIYIKGDSK

EVQSADFTFT GVVKAPFYKD GKWQHDLNSP APLGELESAS

FVYTTPKKNL NASNYTGGLE QFANDLDTFA SSMNDFYGRD

SEDGKHRMFT YKNLPGHKHR FANDVQISIG DAHSGYPVMN

SSFSPNSTTL PTTPLNDWLI WHEVGHNAAE TPLTVPGATE

VANNVLALYM QDRYLGKMNR VADDITVAPE YLEESNGQAW

ARGGAGDRLL MYAQLKEWAE KNFDIKKWYP DGTPLPEFYS

EREGMKGWNL FQLMHRKARG DEVSNDKFGG KNYCAESNGN

AADTLMLCAS WVAQTDLSEF FKKWNPGANA YQLPGASEMS

FEGGVSQSAY NTLASLDLPK PEQGPETINQ VTEHKMSAE
```

Unique to H10407 compared to other E. coli

TABLE 1

Identified Tryptic glycopeptides using BEMAP combined with ESI-MS/MS (SEQ ID NOs: 2-7 and SEQ ID NO: 24-50; glycosylations in bold):

| Start | End | Seq | Mod AA #1 | Mod AA #2 | Mod AA #3 | Mod AA #4 | Mod AA #5 | Mod AA #6 | Mod AA #7 |
|---|---|---|---|---|---|---|---|---|---|
| 355 | 364 | YSTTGQNNTR (SEQ ID NO: 2) | S356 | T57 | T58 | T63 | | | |
| 609 | 615 | YLSNDR (SEQ ID NO: 3) | S612 | | | | | | |
| 588 | 609 | DGQCTLNSDPDDMKNFMENVLR (SEQ ID NO: 4) | S595 | | | | | | |
| 1341 | 1362 | VADDITVAPEYLEESNGQAWAR (SEQ ID NO: 5) | S1355 | | | | | | |
| 1048 | 1076 | VDVEKYPGVVNTNGETVTQNINLYSAPTK (SEQ ID NO: 6) | T1059 | T1063 | T1065 | | | | |

TABLE 1-continued

Identified Tryptic glycopeptides using BEMAP combined with ESI-MS/MS (SEQ ID NOs: 2-7 and SEQ ID NO: 24-50; glycosylations in bold):

| Start | End | Seq | Mod AA #1 | Mod AA #2 | Mod AA #3 | Mod AA #4 | Mod AA #5 | Mod AA #6 | Mod AA #7 |
|---|---|---|---|---|---|---|---|---|---|
| 102 | 143 | VTGATCNGESSDGFTFKPGEDVTCVAGNTTIATFNTQSEAAR (SEQ ID NO: 7) | T103 | T106 | S111 | S112 | T116 | T124 | T130 |
| 91 | 101 | TGYLTLGGSQR (SEQ ID NO: 24) | S99 | | | | | | |
| 144 | 167 | SLRAVEKVSFSLEDAQELAGSDDK (SEQ ID NO: 25) | S144 | | | | | | |
| 169 | 199 | SNAVSLVTSSNSCPANTEQVCLTFSSVIESK (SEQ ID NO: 26) | S177 | S180 | T185 | T191 | | | |
| 218 | 231 | LVNEEVENNAATDK (SEQ ID NO: 27) | T229 | | | | | | |
| 419 | 435 | EIDTAICAKTDGCNEAR (SEQ ID NO: 28) | T422 | | | | | | |
| 428 | 442 | TDGCNEARWFSLTTR (SEQ ID NO: 29) | T428 | S438 | T440 | T441 | | | |
| 456 | 468 | LWGVDTNYKSVSK (SEQ ID NO: 30) | S467 | | | | | | |
| 469 | 486 | FHVFHDSTNFYGSTGNAR (SEQ ID NO: 31) | S476 | | | | | | |
| 487 | 504 | GQAVVNISNAAFPILMAR (SEQ ID NO: 32) | S494 | | | | | | |
| 622 | 636 | SSMTVGTNLETVYFK (SEQ ID NO: 33) | S622 | S623 | T625 | T632 | | | |
| 705 | 719 | LTQQDVTDLIAYMNK (SEQ ID NO: 34) | T711 | | | | | | |
| 720 | 734 | GGSVLIMENVMSNLK (SEQ ID NO: 35) | S722 | | | | | | |
| 735 | 743 | EESASGFVR (SEQ ID NO: 36) | S739 | | | | | | |

TABLE 1-continued

Identified Tryptic glycopeptides using BEMAP combined with ESI-MS/MS (SEQ ID NOs: 2-7 and SEQ ID NO: 24-50; glycosylations in bold):

| Start | End | Seq | Mod AA #1 | Mod AA #2 | Mod AA #3 | Mod AA #4 | Mod AA #5 | Mod AA #6 | Mod AA #7 |
|---|---|---|---|---|---|---|---|---|---|
| 757 | 769 | SVVNNDPQGYPDR (SEQ ID NO: 37) | S757 | | | | | | |
| 818 | 830 | LEVASWQEEVEGK (SEQ ID NO: 38) | S822 | | | | | | |
| 845 | 853 | TPESLAAAK (SEQ ID NO: 39) | S848 | | | | | | |
| 909 | 922 | AMLQAADLGTNIQR (SEQ ID NO: 40) | T918 | | | | | | |
| 923 | 935 | LYQHELYFRTNGR (SEQ ID NO: 41) | T932 | | | | | | |
| 936 | 947 | QGERLNSVDLER (SEQ ID NO: 42) | S942 | | | | | | |
| 948 | 963 | LYQNMSVWLWNETKYR (SEQ ID NO: 43) | T960 | | | | | | |
| 1000 | 1015 | KSLIDNKMIYGEESSK (SEQ ID NO: 44) | S1001 | S1013 | S1014 | | | | |
| 1016 | 1034 | AGMMNPSYPLNYMEKPLTR (SEQ ID NO: 45) | S1022 | | | | | | |
| 1101 | 1120 | STVPVTVTVALADDLTGREK (SEQ ID NO: 46) | T1102 | T1106 | T1116 | | | | |
| 1134 | 1142 | TYDLKANDK (SEQ ID NO: 47) | T1134 | | | | | | |
| 1134 | 1146 | TYDLKANDKTVTFK (SEQ ID NO: 48) | T1144 | | | | | | |
| 1143 | 1160 | VTFKVPYGGLIYIKGDSK (SEQ ID NO: 49) | S1159 | | | | | | |
| 1418 | 1431 | ARGDEVSNDKFGGK (SEQ ID NO: 50) | S1424 | | | | | | |

Identified YghJ glycopeptides listed as probable epitopes presented by Antigen Presenting Cells (SEQ ID NOs: 8-23, glycosylations in bold):

```
QLIHRYSTTGQNN

IHRYSTTGQNNTR

TTGQNNTRVVPDD

NVLRYLSNDRWLP

GQCTLNSDPDDMK

PEYLEESNGQAWA

YPGVVNTNGETVT

VNTNGETVTQNIN

TNGETVTQNINLY

GGSQRVTGATCNG

QRVTGATCNGESS

ATCNGESSDGFTF

TCNGESSDGFTFK

ESSDGFTFKPGED

KPGEDVTCVAGNT

TCVAGNTTIATFN
```

Example 2—Immunogenicity of ETEC Glycosylated Proteins

An immunogenic polypeptide is defined as a polypeptide that induces an immune response.

The immune response may be monitored by one of the following methods:

An in vitro cellular response is determined by release of a relevant cytokine such as IFN-γ, from lymphocytes withdrawn from an animal or human currently or previously infected with ETEC, or by detection of proliferation of these T cells. The induction is performed by addition of the polypeptide or the immunogenic part to a suspension comprising from $1\times10^5$ cells to $3\times10^5$ cells per well. The cells are isolated from either blood, the spleen, the liver or the lung and the addition of the polypeptide or the immunogenic part of the polypeptide result in a concentration of not more than 20 µg per ml suspension and the stimulation is performed from two to five days. For monitoring cell proliferation, the cells are pulsed with radioactive labeled Thymidine and after 16-22 hours of incubation, the proliferation is detected by liquid scintillation counting. A positive response is a response more than background plus two standard deviations. The release of IFN-γ can be determined by the ELISA method, which is well known to a person skilled in the art. A positive response is a response more than background plus two standard deviations. Other cytokines than IFN-γ could be relevant when monitoring an immunological response to the polypeptide, such as IL-12, TNF-α, IL-4, IL-5, IL-10, IL-6, TGF-β.

Another and more sensitive method for determining the presence of a cytokine (e.g. IFN-γ) is the ELISPOT method where the cells isolated from either the blood, the spleen, the liver or the lung are diluted to a concentration of preferable of 1 to $4\times10^6$ cells/ml and incubated for 18-22 hrs in the presence of the polypeptide or the immunogenic part of the polypeptide resulting in a concentration of not more than 20 µg per ml.

The cell suspensions are hereafter diluted to 1 to $2\times10^6$/ml and transferred to Maxisorp MaxiSorp™ plates coated with anti-IFN-γ and incubated for preferably 4 to 16 hours. The IFN-γ producing cells are determined by the use of labelled secondary anti-IFN-antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or an ETEC infected person where the T cell lines have been driven with either live ETEC, extracts from the bacterial cell or culture filtrate for 10 to 20 days with the addition of IL-2. The induction is performed by addition of not more than 20 µg polypeptide per ml suspension to the T cell lines containing from $1\times10^5$ cells to $3\times10^5$ cells per well and incubation is performed from two to six days. The induction of IFN-γ or release of another relevant cytokine is detected by ELISA. The stimulation of T cells can also be monitored by detecting cell proliferation using radioactively labeled Thymidine as described above. For both assays, a positive response is a response more than background plus two standard deviations.

An in vivo cellular response may be determined as a positive DTH response after intradermal injection or local application patch of at most 100 µg of the polypeptide or the immunogenic part to an individual who is clinically or subclinically infected with ETEC, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic part is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the presence or absence of a specific label e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of an ETEC. Readout for induced protection could be decrease of the bacterial load in target organs compared to non-vaccinated animals, prolonged survival times compared to non-vaccinated animals and diminished weight loss or pathology compared to non-vaccinated animals.

The glycosylated polypeptides described herein are immunogenic when one of the above-described tests is positive.

Example 3—Schematic Overview of Assays and Experiments Used to Characterize Glycosylated as Well as Non-Glycosylated YghJ Protein Properties

TABLE 2

Type of experiment

Mouse challenge
Serum and mucosal antibody responses
Antibody mediated inhibition of ETEC binding to Caco-2
Antibody mediated inhibition of ETEC binding to Caco-2; cAMP release measurement
Degradation of intestinal mucin MUC3
Quantitative YghJ - MUC3 interaction assessment
Degradation of intestinal mucin MUC2

An overview of the assays used for testing a wide variety of YghJ features is given in Table 2.

Example 4—Vaccination with Glycosylated YghJ Affords Better Protection Against Intestinal Colonization of ETEC in Mice Compared to the Non-Glycosylated Protein Versions Assay Type: Mouse Challenge Studies
Materials and Methods:
Seven groups of CD-1 mice were immunized with either adjuvant only (control), or appropriate amount of adjuvant+ 25 µg of glycosylated YghJ or adjuvant+e.g. 25 µg of non-glycosylated YghJ on days 0, 14, 28. On day 40, mice were treated with streptomycin [e.g. 5 g per liter] in drinking water for 24 hours, followed by drinking water alone for 18 hours. After administration of famotidine to reduce gastric acidity, mice were challenged with 106 cfu of a chloramphenicol-resistant ETEC strain by oral gavage. Fecal samples (6 pellets/mouse) were collected on day 42 before oral gavage, re-suspended in buffer (10 mM Tris, 100 mM NaCl, 0.05% TWEEN® 20 (polysorbate 20), 5 mM Sodium Azide, pH 7.4) overnight at 4° C., centrifuged to pellet insoluble material, and recover supernatant for fecal antibody testing (below). Twenty-four hours after infection, mice were sacrificed, sera were collected, and dilutions of saponin small-intestinal lysates were plated onto Luria agar plates containing chloramphenicol (40 µg/ml).
Experimental outcome: As determined by CFU counting, fecal samples from mice immunized with glycosylated antigen YghJ contained fewer ETEC compared to fecal samples from mice immunized with non-glycosylated antigen versions.

Example 5—Immunization with Glycosylated Antigen YghJ Generates Robust Serum and Mucosal Antibody Responses Assay Type: ELISA Assay Probing Relative Levels of IgA, IgM and IgG
Materials and Methods:
Murine immune responses to adjuvant, glycosylated and non-glycosylated versions of YghJ were determined using ELISA. Briefly, ELISA wells were incubated at 4° C. overnight with proteins at a final concentration of 4 µg/ml in 0.1 M NaHCO3 buffer (pH 8.6), washed the following day with Tris-buffered saline containing 0.005% TWEEN® 20 (polysorbate 20) (TBS-T), and blocked with 1% bovine serum albumin (BSA) in TBS-T for 1 h at 37° C. prior to the addition of the samples. Sera was serial diluted in TBS-T with 1% BSA, and 100 µl was added to each ELISA well, followed by incubation at 37° C. for 1 h. After three washes with TBS-T, horseradish peroxidase-conjugated secondary antibody (either goat anti-mouse IgA, IgM, or IgG) was added at a final dilution of 1:5,000, followed by incubation for an additional hour before washing and development with TMB (3,3',5,5'-tetramethylbenzidine)-peroxidase substrate (KPL). Kinetic ELISA data are expressed as Vmax in milliunits/min.
Experimental outcome: Immunization with glycosylated antigen YghJ generates robust IgA, IgG and IgM antibody responses as compared to non-glycosylated versions Example 6—Monoclonal Antibodies Raised Against Glycosylated YghJ Inhibits ETEC Binding to Intestinal Epithelial Cells to a Higher Extent Compared Monoclonal Antibodies Raised Against Non-Glycosylated YghJ Protein Version Assay Type: Adhesion Assay
Materials and Methods:
In vitro, Caco-2 epithelial cell monolayers were infected with ETEC H10407 at multiplicities of infection of approximately 100 (bacteria/cell). Cultures of bacteria were grown overnight in Luria broth from frozen glycerol stocks, diluted 1:100, and grown for 1 h. One microliter of bacterial culture is added to confluent Caco-2 monolayers seeded into 96-well plates preincubated with or without antibodies. Two hours after inoculation, the monolayers were washed 3 times with tissue culture medium after which bacteria were isolated, serial diluted and plated to count CFU the following day.
Experimental outcome: Monoclonal antibodies raised against glycosylated YghJ inhibits ETEC binding to intestinal epithelial cells to a higher extent compared monoclonal antibodies raised against non-glycosylated YghJ protein version.

Example 7—Monoclonal Antibodies Raised Against Glycosylated YghJ Inhibits ETEC Binding to Intestinal Epithelial Cells to a Higher Extent Compared to Monoclonal Antibodies Raised Against Non-Glycosylated YghJ Protein Version Assay Type: Adhesion Assay Coupled to cAMP Enzyme Immunoassay
Materials and Methods:
In vitro, Caco-2 epithelial cell monolayers were infected with ETEC H10407 at multiplicities of infection of approximately 100 (bacteria/cell). Cultures of bacteria were grown overnight in Luria broth from frozen glycerol stocks, diluted 1:100, and grown for 1 h. One microliter of bacterial culture is added to confluent Caco-2 monolayers seeded into 96-well plates preincubated with or without antibodies. Two hours after inoculation, the monolayers were washed 3 times with tissue culture medium, and the medium was replaced with 100 µl of fresh medium/well and returned to the incubator (37° C., 5% $CO_2$) for 2.5 h. Subsequently, cyclic AMP (cAMP) enzyme immunoassay (EIA) (Arbor Assays, Ann Arbor, Mich.) was used to examine the efficiency of toxin delivery.
Experimental outcome: Addition of antibodies raised against glycosylated YghJ results in lower levels of released cAMP into the growth medium compared to monoclonal antibodies raised against non-glycosylated YghJ protein version.

Example 8—Glycosylated YghJ Degrade Intestinal Mucin MUC3 in a Dose-Dependent Fashion to a Higher Extent Compared to the Non-Glycosylated YghJ Protein Version and Mucin Degrading Activity can be Blocked with Monoclonal Antibodies Targeting Glycosylated Epitopes Assay Type: Western Blot
Materials and Methods:

To examine the activity of glycosylated and non-glycosylated YghJ against the cell-associated mucin MUC3, Caco-2 epithelial cells were grown in monolayers in 96-well tissue culture plates for 48 to 72 h postconfluence to optimize MUC3 expression on the epithelial surface. Supernatant was removed and replaced with 100 µl of minimum essential medium (MEM) containing YghJ (+/−glycosylation; final concentration of 1-500 µg/ml) either with or without aliquots of antibody. Following overnight treatment of the cell monolayers at 37° C. and 5% $CO_2$, the medium was removed, and the monolayers were lysed in 20 µl of lysis buffer (e.g. 50 mM sodium phosphate, 250 mM NaCl, 0.1% Triton X-100, 0.1 mM phenylmethylsulfonyl fluoride [PMSF], and complete EDTA-free protease inhibitor cocktail [Roche]). Following incubation on ice for 30 min and repeated freeze (dry ice)-thaw (37° C.) cycles, the lysates were centrifuged at 10,000×g (4° C.) to pellet debris. Clarified lysates were then separated on gradient (3 to 8% Tris-acetate; Invitrogen) PAGE. Following transfer to nitrocellulose membranes, Caco-2 lysates were immunoblotted with anti-MUC3A/B goat polyclonal IgG antibodies (F-19 [catalog no. sc-13314; Santa Cruz]) that recognize an internal region of mucin 3A of human origin (gene identification [ID] 4584).

Experimental outcome: As determined by Western blotting, Caco-2 cells exposed to glycosylated YghJ displays higher extent of MUC3 degradation compared to cells incubated with the non-glycosylated protein variant. Moreover, the proteolytic activity of YghJ can be blocked by adding monoclonal antibodies targeting the glycosylated amino acids.

Example 9—Glycosylated YghJ Interacts Stronger with the Human Intestinal Mucin, MUC3, Compared to the Non-Glycosylated YghJ Protein Version Assay Type: Far Western Blot
Materials and Methods To examine interaction of YghJ with the human intestinal mucin MUC3, lysate from Caco-2 cells containing MUC3 was separated by SDS-PAGE as described above and transferred to nitrocellulose membranes. To examine interaction with MUC3, purified protein was spotted on nitrocellulose membranes. Far Western analysis was then performed with purified YghJ 3×FLAG. Briefly, nitrocellulose membranes with immobilized mucins were blocked for 1 h with 1% bovine serum albumin (BSA) in PBS before incubating with 50 µg/ml of purified YghJ (+/−glycosylations) overnight at 4° C. Proteins were detected by immunoblotting using antimucin antibodies or anti-YghJ monoclonal antibody obtained from mice.

Expected outcome: When exposing immobilized MUC3 to either glycosylated YghJ or the non-glycosylated protein variant, Far Western blotting shows that the modified YghJ exhibits stronger binding towards the mucin.

Example 10—Glycosylated YghJ Degrade Purified Intestinal Mucin MUC2 in a Dose-Dependent Fashion to a Higher Extent Compared to the Non-Glycosylated YghJ Protein Version and Mucin Degrading Activity can be Blocked with Affinity Purified Antibodies Assay Type: Western Blot
Materials and Methods MUC2 was purified from supernatants of tissue culture medium from LS174T cells (ATCC CL-188), a goblet cell-like adenocarcinoma line that makes abundant MUC2. Briefly, LS174T cells were grown as described above; conditioned medium was recovered, concentrated by ultrafiltration using a 100-kDa-molecular-weight-cutoff filter (MWCO), and then buffer exchanged with 10 mM Tris-HCl and 250 mM NaCl (pH 7.4) prior to size exclusion chromatography using Sepharose CL-2B resin. Fractions were checked for MUC2 by anti-MUC2 dot immunoblotting. MUC2-positive fractions, corresponding to a protein peak in the column void volume, were separated on 3 to 8% Tris-acetate gradient gels, stained with SYPRO® Ruby to check purity, and immunoblotted using anti-MUC2 to verify the identity of the protein. Fractions containing intact, full-length MUC2 were then pooled and saved at −80° C. for subsequent assays.

To examine degradation of purified MUC2, 0.1 µg of protein was treated for at least 30 min with 5 µg of either glycosylated or non-glycosylated YghJ at 37° C. Affinity purified antibodies, isolated from rat exposed to either the glycosylated or non-glycosylated antigen, was added to reaction mixture in order to inhibit MUC2 degradation. Reaction products were resolved by SDS-PAGE or agarose gels optimized for protein separation, and MUC2 digests were examined with anti-MUC2 rabbit polyclonal (IgG) (H-300 [catalog no. sc-15334; Santa Cruz]) that recognizes an epitope corresponding to amino acids 4880 to 5179 at the C terminus of human mucin 2 (gene ID 4583).

Expected outcome: The degradation rate of purified intestinal mucin MUC2 is higher when exposed to glycosylated YghJ as compared to non-glycosylated YghJ. Furthermore, mucin degradation can be blocked with affinity-purified YghJ antibodies.

REFERENCES

Thingholm et al. (2006), Nat. Protoc. 1, 1929-1935
Knudsen et al. (2008), Biochem. J. 412, 563-577
Chou and Schwartz (2011), Curr. Protoc. Bioinformatics, chapter 13, 15-24
Pearson and Lipman (1988), Proc. Natl. Acad. Sci. 85, 2444-2448.
Thompson et al. (1994), Nucleic Acids Res. 11, 4673-4680.

The invention claimed is:

1. A method for identifying and/or mapping O-linked glycoproteins, the method comprising the following steps:
   i) provision of a sample comprising an O-linked glycoprotein,
   ii) substitution of any O-linked carbohydrate moieties with a 2-Aminoethyl phosphonic acid (AEP) group,
   iii) TiO$_2$ enrichment of the 2-AEP-tagged glycoprotein, and
   iv) mass spectrometry of the enriched 2-AEP-tagged glycoprotein.

2. The method according to claim 1, wherein said substitution comprises contacting said sample with a substitution solution comprising 2-AEP, NaOH and Ba(OH)$_2$.

3. The method according to claim 2, wherein the substitution solution comprises 0.4 M 2-AEP, 0.75 M NaOH and 20 mM Ba(OH)$_2$.

4. The method according to claim 1, wherein said substitution is performed at 37° C. for at least 3 hours.

5. The method according to claim 1, wherein the substitution reaction is stopped prior to step iii) by addition of an acid.

6. The method according to claim 5, wherein the acid is trifluoroacetic acid (TFA).

7. The method according to claim 6, wherein TFA is added to a final concentration of TFA of 1%.

8. The method according to claim 1, wherein in step ii) the efficiency of replacement of carbohydrate moieties with 2-AEP is at least 95%.

9. The method according to claim 1, wherein mass spectrometry is selected from the group consisting of tandem mass spectrometry (MS/MS), matrix-assisted laser desorption/ionization (MALDI) and Electrospray ionization (ESI)-MS/MS.

10. The method according to claim 9, wherein mass spectrometry is tandem mass spectrometry (MS/MS).

11. The method according to claim 10, wherein fragmentation of molecules for tandem mass spectrometry (MS/MS) is achieved by collision-induced dissociation (CID) or higher-energy collisional dissociation (HCD).

12. The method according to claim 1, wherein the sample is treated with alkaline phosphatase prior to step ii).

13. The method according to claim 1, wherein said sample is provided as a lyophilized peptide sample.

14. The method according to claim 13, wherein said substitution comprises resuspending said lyophilized peptide sample in said substitution solution.

15. The method according to claim 1, wherein the O-linked glycoproteins are glycosylated in at least two positions.

16. The method according to claim 1, wherein the O-linked glycoproteins are hyperglycosylated.

* * * * *